(12) United States Patent
Larkin

(10) Patent No.: US 8,262,673 B2
(45) Date of Patent: Sep. 11, 2012

(54) AMNIOTOMY DEVICE AND ASSEMBLY

(76) Inventor: Daniel Larkin, St. Paul, MN (US)

( * ) Notice: Subject to any disclaimer, the term of this patent is extended or adjusted under 35 U.S.C. 154(b) by 545 days.

(21) Appl. No.: 12/431,561

(22) Filed: Apr. 28, 2009

(65) Prior Publication Data

US 2009/0209974 A1 Aug. 20, 2009

Related U.S. Application Data

(63) Continuation-in-part of application No. 12/126,143, filed on May 23, 2008.

(60) Provisional application No. 60/981,292, filed on Oct. 19, 2007.

(51) Int. Cl.
*A61B 17/42* (2006.01)

(52) U.S. Cl. ........................................... 606/125

(58) Field of Classification Search .................. 600/201, 600/206, 208, 210, 226; 606/96, 119, 125, 606/190, 191; 407/54; D15/139
See application file for complete search history.

(56) References Cited

U.S. PATENT DOCUMENTS

| | | | |
|---|---|---|---|
| 2,847,012 A | 8/1958 | Eastman | |
| 3,336,611 A * | 8/1967 | Schepp | 7/158 |
| 3,533,411 A | 10/1970 | McKnight | |
| 3,587,591 A | 6/1971 | Satterwhite | |
| 3,867,947 A | 2/1975 | Schack | |
| 4,100,923 A | 7/1978 | Southern | |
| 4,285,618 A * | 8/1981 | Shanley, Jr. | 407/54 |
| 4,357,945 A | 11/1982 | Janko | |
| 4,662,376 A | 5/1987 | Belanger | |
| 5,087,262 A | 2/1992 | Sheahon | |
| 6,409,734 B1 | 6/2002 | Zapata | |
| 2002/0007186 A1 | 1/2002 | Zapata | |
| 2005/0065543 A1 | 3/2005 | Kahle et al. | |
| 2005/0251170 A1 | 11/2005 | Weisenburgh, II et al. | |

OTHER PUBLICATIONS

Non-Final Office Action mailed for U.S. Appl. No. 12/126,143 (16 pages).

* cited by examiner

*Primary Examiner* — Ryan Severson
*Assistant Examiner* — Ashley Cronin
(74) *Attorney, Agent, or Firm* — Dicke, Billig & Czaja, PLLC

(57) ABSTRACT

An amniotomy device includes a shaft having a rupture crown disposed along a distal end portion of the shaft. The rupture crown includes a distal end defined by at least two leading bite wings and a recess formed in the distal end of the rupture crown between the leading bite wings. The leading bite wings are configured to engage amniotic membrane when the shaft is rotated and rupture the amniotic membrane.

19 Claims, 19 Drawing Sheets

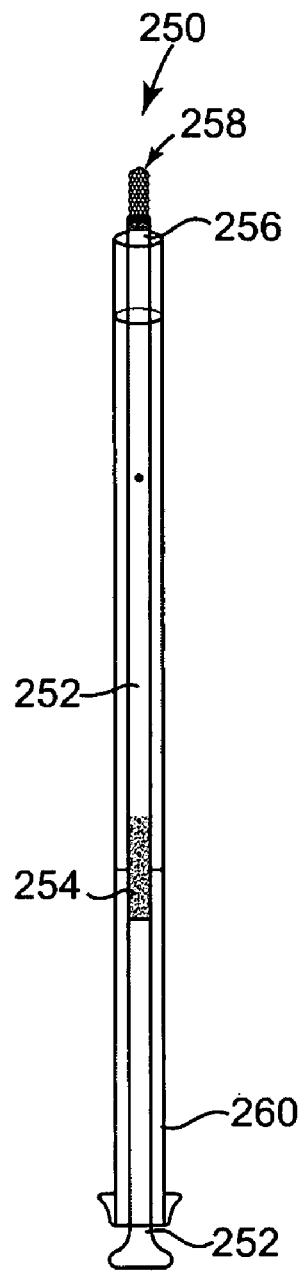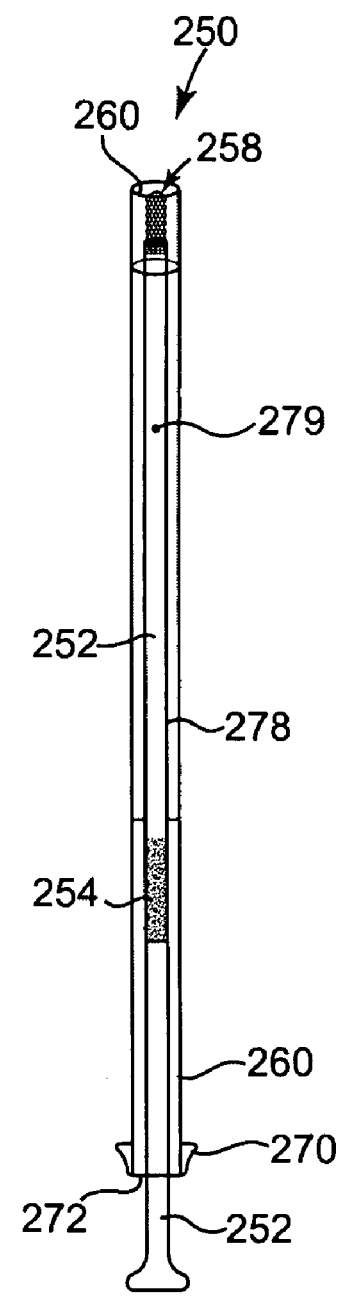
Fig. 9A
Fig. 9B

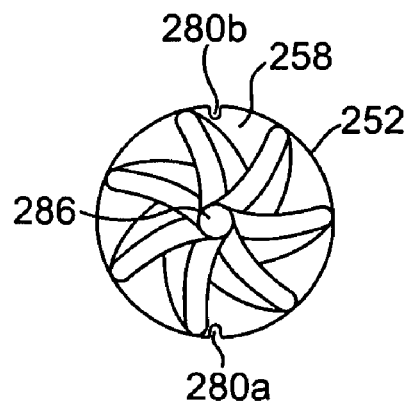 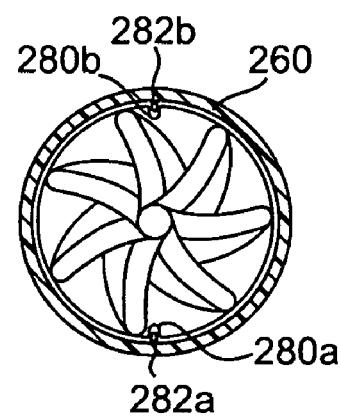
Fig. 11A   Fig. 11B
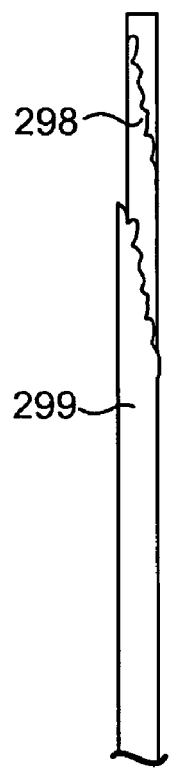 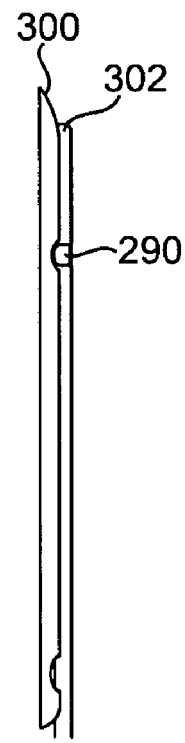
Fig. 12A   Fig. 12B

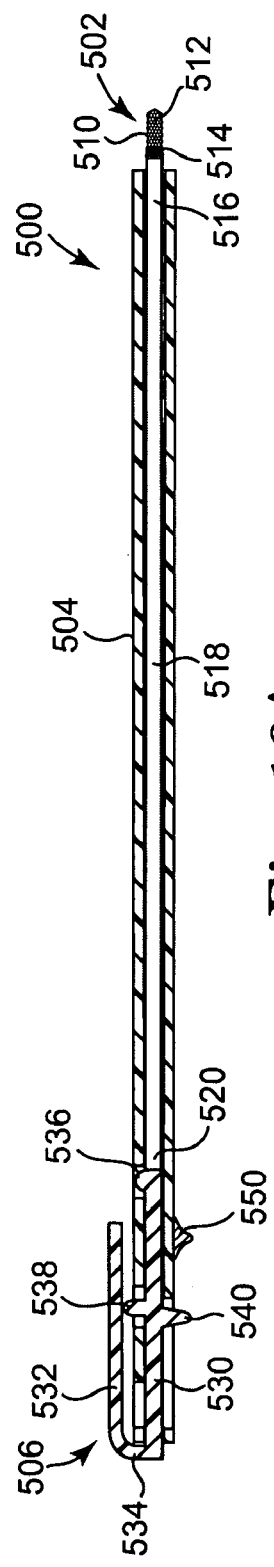
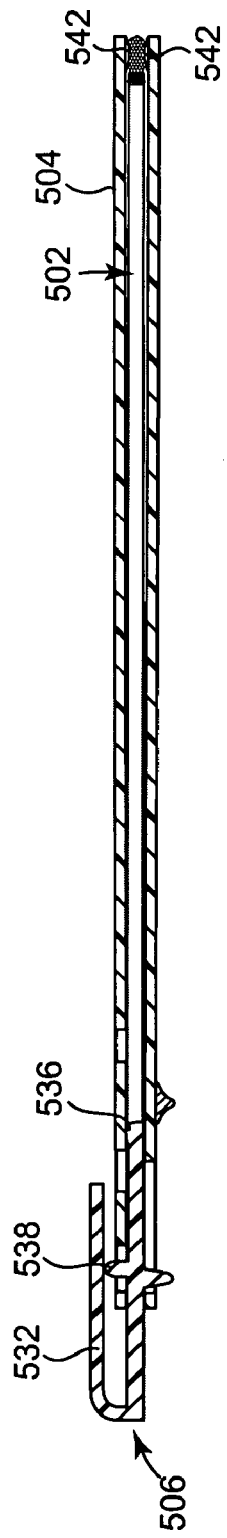
Fig. 16A
Fig. 16B

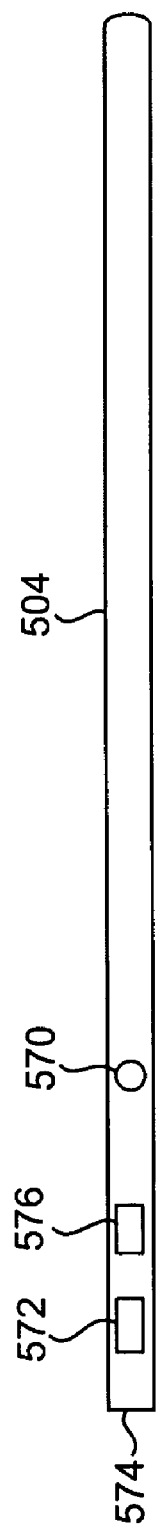
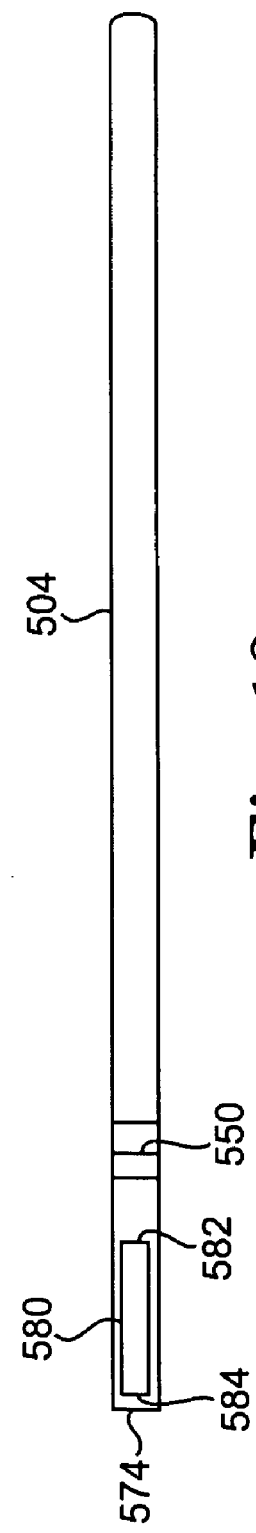

AMNIOTOMY DEVICE AND ASSEMBLY

CROSS-REFERENCE TO RELATED APPLICATION

This Non-Provisional patent application is a Continuation-in-Part and claims the benefit of the filing date of Non-Provisional patent application Ser. No. 12/126,143 filed May 23, 2008, entitled "AMNIOTOMY DEVICE," which claimed the benefit of the filing date of U.S. Provisional Patent Application Ser. No. 60/981,292 filed Oct. 19, 2007, entitled "AMNIOTOMY DEVICE."

BACKGROUND

The amniotic sac is a pair of membranes that enclose a developing embryo as it develops to a fetus. The amniotic sac includes an inner membrane called the amnion that contains the amniotic fluid and the fetus, and an outer membrane called the chorion that contains the amnion and a portion of the placenta. Amniotomy is the artificial rupture of membranes (AROM) that is usefully employed to induce and/or accelerate labor.

U.S. Pat. No. 4,662,376 provides an amniotomy instrument that includes a curved tube having a handle and a suction piston movably mounted within the tube. The tube terminates in a bell-shaped structure at a distal end, and includes piercing pins mounted within the tube. The piercing pins are positioned such that they cannot contact the fetus even as the amniotic sac is drawn into the tube. The instrument is configured for two-hand operation by an attending physician, where the piston is retracted within the tube, and a portion of the amniotic sac is drawn into the distal end of the tube to be pierced by the piercing pins.

U.S. Pat. No. 5,968,055 provides another amniotomy instrument. The instrument includes a curved elongated shaft having a distal end, where the distal end includes a rounded structure curved over a sharp, pointed hook. During use, the attending physician positions an index finger along the rounded structure to guide the sharp pointed hook to the amniotic sac. When in position, the hook is engaged with the amniotic sac to perforate the membranes.

Although generally effective and useful, the known AROM devices are not suited for access through a minimally dilated, relatively closed cervix. Improvements to the devices employed to perforate the amniotic sac would be welcomed by obstetric physicians and their patients.

SUMMARY

One aspect provides an amniotomy device including a shaft having a rupture crown disposed along a distal end portion of the shaft. The rupture crown includes a distal end defined by at least two leading bite wings and a recess formed in the distal end of the rupture crown between the leading bite wings. The leading bite wings are configured to engage amniotic membrane when the shaft is rotated and rupture the amniotic membrane.

BRIEF DESCRIPTION OF THE DRAWINGS

The accompanying drawings are included to provide a further understanding of the disclosure and are incorporated in as a part of this specification. The drawings illustrate example embodiments and together with the description serve to explain principles of the invention. Other embodiments and many of the intended advantages of the embodiments will be readily appreciated as they become better understood by reference to the following detailed description. The elements of the drawings are not necessarily to scale relative to each other. Like reference numerals designate corresponding similar parts.

FIG. 9A is a side view of an amniotomy device including a crown and a sleeve retracted to expose the crown according to one embodiment.

FIG. 9B is a side view of the amniotomy device shown in FIG. 9A illustrating the sleeve deployed over the crown.

FIG. 11A is a top view of the crown of the amniotomy device shown in FIG. 9A.

FIG. 11B is a top view of the amniotomy device shown in FIG. 9A including the crown and the sleeve disposed around the crown.

FIG. 12A is a side view of a cutting edge configured for attachment to the sleeve shown in FIG. 10A according to one embodiment.

FIG. 12B is a side view of another cutting edge configured for attachment to the sleeve shown in FIG. 10A according to one embodiment.

FIG. 16A is a cross-sectional view of an amniotomy assembly including an advancer attached to an amniotomy device that is insertable into a protective sleeve according to one embodiment.

FIG. 16B is a cross-sectional view of the amniotomy assembly shown in FIG. 16A illustrating a rupture crown protectively disposed within the protective sleeve.

FIG. 17 is a top view of the protective sleeve shown in FIG. 16A.

FIG. 18 is a bottom view of the protective sleeve shown in FIG. 16A.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Embodiments provide an obstetrical instrument configured to rupture amniotic membranes of a pregnant woman to release the amniotic fluid retained by the membranes, and thus to induce labor prematurely and facilitate delivery and/or to reduce the internal pressure within the uterus.

Figures 1A, 1B:
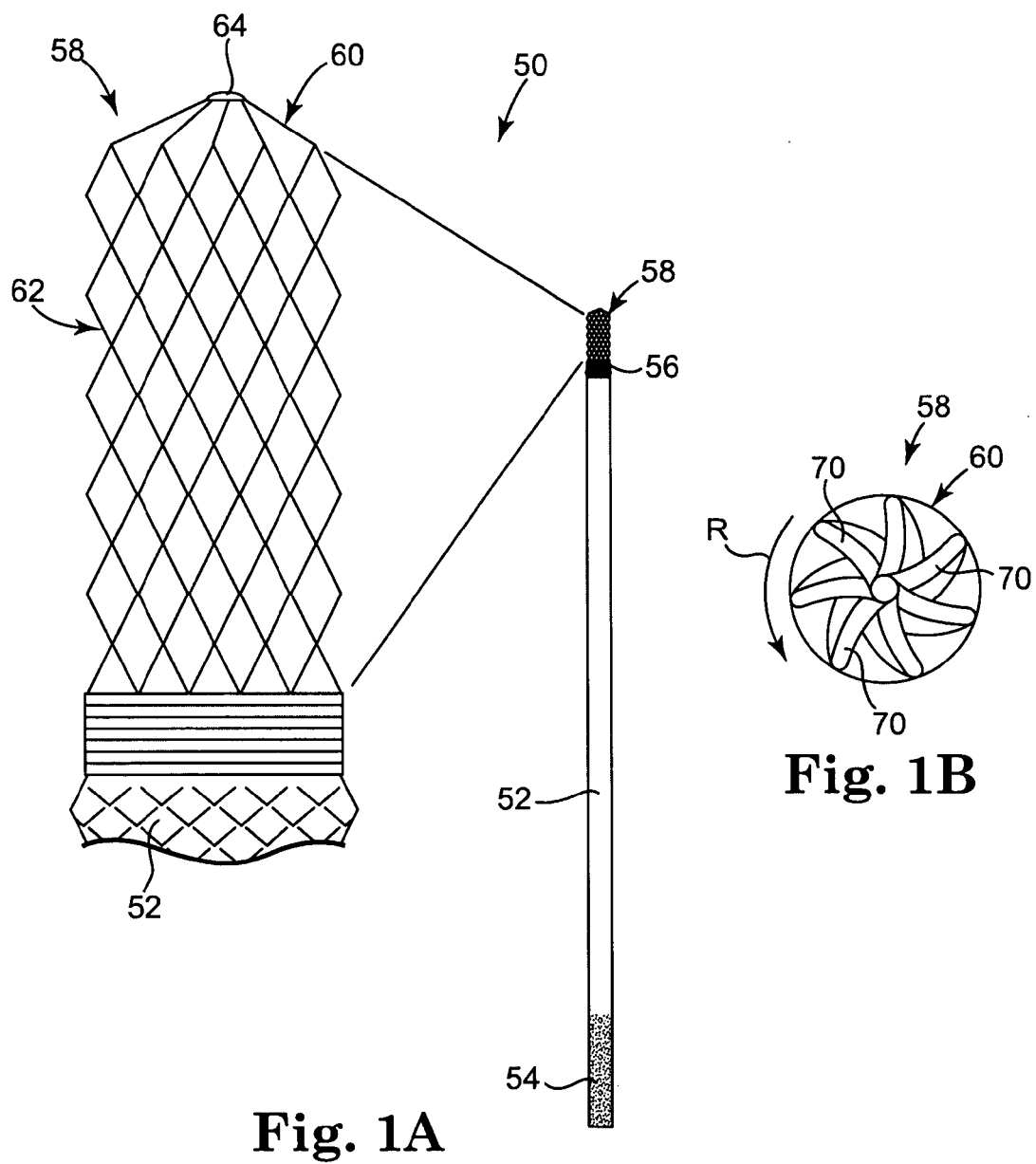
FIG. 1A is a front view of an amniotomy device and a macroscopic front view of a crown of the amniotomy device according to one embodiment.
FIG. 1B is a top view of the crown shown in FIG. 1A.

FIG. 1A is a front view of an amniotomy device 50 and a macroscopic front view of a crown 58 of the amniotomy device 50 according to one embodiment. Amniotomy device 50 includes a shaft 52 defining a proximal end 54, a distal end 56 separated from proximal end 54, and a crown 58 disposed on distal end 56. Crown 58 includes a first set of leading bite wings 60 formed on a distal surface of crown 58, a second set of trailing bite wings 62 formed on a side surface of crown 58, and a third set of trailing bite wings 63 disposed between bite wings 62 and proximal end 54.

In one embodiment, shaft 52 is substantially linear and characterized by an absence of curvature along a longitudinal axis of shaft 52. Shaft 52 is configured to access a minimally dilated and relatively closed cervix. The absence of curvature of shaft 52 enables shaft 52 to directly approach the amniotic sac without unduly pressing against the tissue of the vaginal vault and/or the cervix during insertion and/or use. Shaft 52 includes a textured and/or knurled surface adjacent proximal end 54 configured to facilitate rotation of shaft 52 during use.

In one embodiment, the first set or flight of leading bite wings 60 is configured to engage tissue of an amniotic sac when shaft 52 is rotated in a first direction (e.g., clockwise). The uni-directional nature of the bite wings 60 is configured such that bite wings 60 do not engage the tissue of the amniotic sac when shaft 52 is rotated in a second direction opposite the first direction (e.g., counter-clockwise). Leading bite wings 60 are suited for axial insertion through a relatively closed cervix with minimal or no local trauma to the cervical tissue. Bite wings 60 are configured to not cut the amniotic sac tissue upon contact, but are rather configured to engage the tissue of the sac, wrapping the tissue around the crown 58 as shaft 52 is further rotated, until the tissue is drawn into contact with and ruptured by the second set of trailing bite wings 62, as described further below. To this end, bite wings 60 provide one means for engaging/wrapping of the tissue of the amniotic sac about crown 58 when device 50 is rotated.

In one embodiment, second set of trailing bite wings 62 is configured to rupture the amniotic sac as the amniotic sac is drawn down a side of shaft 52 into contact with the second set of trailing bite wings 62. In other words, leading bite wings 60 capture the tissue of the amniotic sac and pull the amniotic sac down into engagement with the trailing bite wings 62. Trailing bite wings 62 are configured to rupture the amniotic sac and release amniotic fluid contained therein to induce labor and/or reduce the internal pressure within the uterus. Thus, trailing bite wings 62 provide one means of rupturing the amniotic sac when device 50 is rotated.

In one embodiment, leading bite wings 60 taper between an apex 64 at a distal end of device 50 down to trailing bite wings 62. In one embodiment, trailing bite wings 62 include a plurality of raised points configured to rupture the amniotic sac. In another embodiment, second set of trailing bite wings 62 is configured to more fully engage the amniotic sac and draw the amniotic sac down the side of shaft 52 into contact with the third set of trailing bite wings 63. Leading bite wings 60 capture the tissue of the amniotic sac, bite wings 62 pull the amniotic sac down into engagement with the trailing bite wings 63, and trailing bite wings 63 are configured to rupture the amniotic sac and release amniotic fluid contained therein to induce labor and/or reduce the internal pressure within the uterus. In one embodiment, third set of trailing bite wings 63 include raised rupture-points that are disposed substantially perpendicular to bite wings 62.

FIG. 1B is a top view of crown 58 according to one embodiment. Leading bite wings 60 include a uni-directional flight of edges 70 configured to engage with the amniotic sac. In particular, flight edges 70 are configured to snag or engage the tissue of the amniotic sac when shaft 52 (FIG. 1A) is rotated in the first direction (the direction of the arrow R). Additional rotation of shaft 52 in the direction of arrow R wraps or transports the tissue of the amniotic sac from a distal end of crown 58 to a proximal end of crown 58. Flight edges 70 are configured to not engage with the amniotic sac when the shaft 52 is rotated in the counter-clockwise direction when the shaft is viewed from the proximal end 54 to the distal end 56.

In one embodiment, shaft 52 is substantially linear, and leading bite wings 60 are configured to not engage with tissue until shaft 52 is rotated, e.g., in a clockwise manner. In this regard, amniotomy device 50 is configured to be inserted into the cervix and maintained at a particular longitudinal position as it is rotated, and is thus particularly well suited for rupturing membranes of the amniotic sac when the cervix is relatively closed. In contrast, the curved amniotomy instruments known in the art are manipulated into and out of the cervix, and are likely to traumatize the walls of a closed cervix as the instruments are maneuvered to rupture the membranes of the amniotic sac. The amniotomy device 50 described herein is configured to provide improved access to a cervix that is dilated less than 2 cm while minimizing the potential for traumatizing the cervical tissue.

In one embodiment, shaft 52 and crown 58 are fabricated from the same material such that the device 50 is suited for autoclaving, steam sterilization, ethylene oxide sterilization, and other forms of surgical instrument cleaning. In one embodiment, amniotomy device 50 is fabricated from stainless steel. In another embodiment, amniotomy device 50 is fabricated from a radio opaque plastic suited for single use disposal medical products.

Figure 2A:
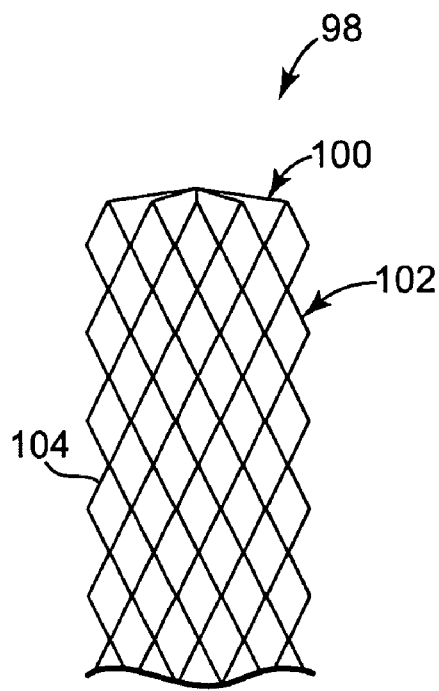
FIG. 2A is a side view of a crown of an amniotomy device according to another embodiment.

FIG. 2A is a side view of a crown 98 of an amniotomy device according to another embodiment. Crown 98 includes a leading bite wing surface 100, and a trailing bite wing surface 102. Similar to the amniotomy device 50 described above, leading bite wing surface 100 is configured to engage with the amniotic sac and draw tissue to trailing bite wing surface 102, and trailing bite wing surface 102 is configured to rupture the amniotic sac. In particular, trailing bite wing surface 102 includes a plurality of cutting serrations 104 disposed along the surface 102 configured to rupture the amniotic sac.

Figure 2B:
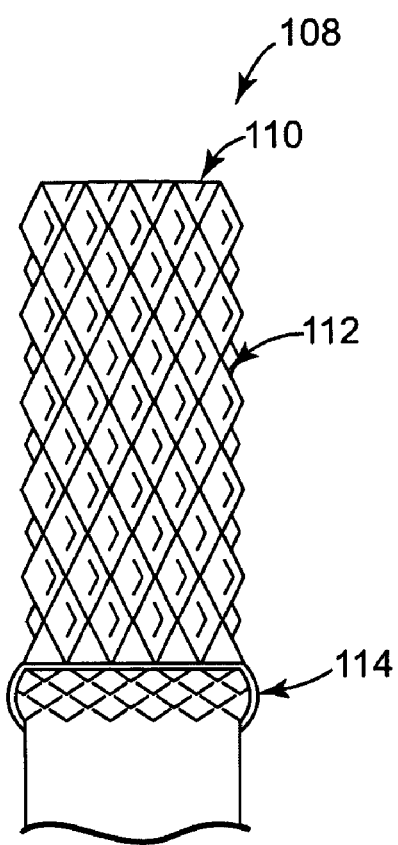
FIG. 2B is a side view of a crown of another amniotomy device according to one embodiment.

FIG. 2B is a side view of a crown 108 of an amniotomy device according to another embodiment. Crown 108 includes a leading bite wing surface 110 configured to engage and draw amniotic sac tissue to a trailing bite wing surface 112, and trailing bite wing surface 112 is configured to rupture the amniotic sac. In one embodiment, crown 108 includes a radial prominence 114 configured to provide a guiding surface for the finger of a physician when approximating the amniotic sac.

Figure 2C:
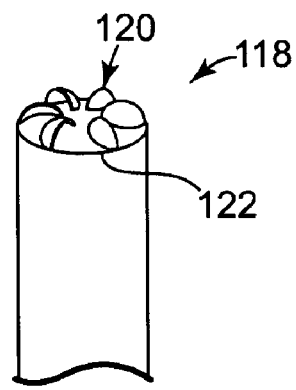
FIG. 2C is a perspective view of a crown of another amniotomy device according to one embodiment.

FIG. 2C is a perspective view of another crown 118 of an amniotomy device according to one embodiment. Crown 118 includes a leading bite wing surface 120 configured to engage and draw amniotic sac tissue to a trailing bite wing 122, and trailing bite wing 122 is configured to rupture the amniotic sac. In one embodiment, the trailing bite wing 122 includes a cutting edge circumscribed along a periphery of crown 118.

Figure 3:
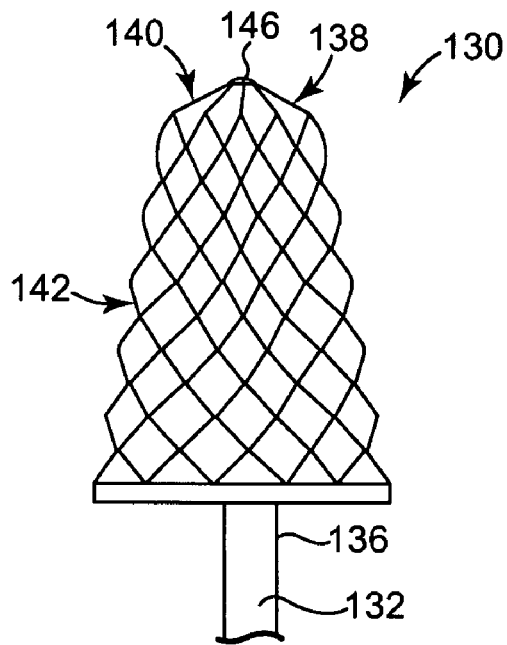
FIG. 3 is a side view of an amniotomy device including a generally conical crown disposed at a distal end of the amniotomy device according to one embodiment.

FIG. 3 is a side view of an amniotomy device 130 according to another embodiment. Amniotomy device 130 includes a shaft 132 and a generally conical crown 138 coupled to a distal end 136 of shaft 132. Crown 138 includes a leading bite wing surface 140 that tapers to a trailing bite wing surface 142, and a blunt distal end 146 that is configured to atraumatically contact sensitive cervical tissue. In one embodiment, trailing bite wing surface 142 defines a plurality of pyramidal-shaped cutting teeth projecting from a side surface of crown 138.

Figure 4:
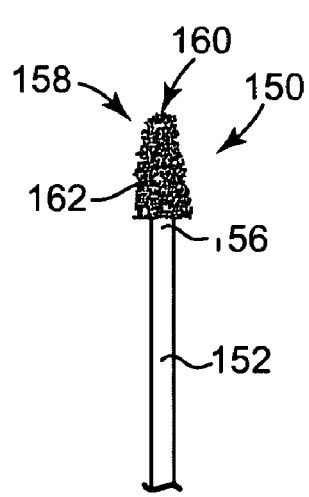
FIG. 4 is a side view of an amniotomy device including a generally conical crown disposed at a distal end of the amniotomy device according to another embodiment.

FIG. 4 is a side view of an amniotomy device 150 according to another embodiment. Amniotomy device 150 includes a shaft 152 and a crown 158 disposed on a distal end 156 of shaft 152. Crown 158 is similar in shape to the generally conical crown 138 (FIG. 3), but includes a greater multiplicity of pin-shaped bite wings disposed on a trailing bite wing surface 162. In one embodiment, crown 158 includes a leading bite wing surface 160 that conically tapers to trailing bite wing surface 162. Similar to the embodiments described above, leading bite wing surface 160 is configured to engage and pull tissue of the amniotic sac, and upon further rotation of shaft 152, to deliver the tissue to trailing bite wing surface 162. Trailing bite wing surface 162 is configured to rupture the amniotic sac as shaft 152 is rotated.

Figure 5:
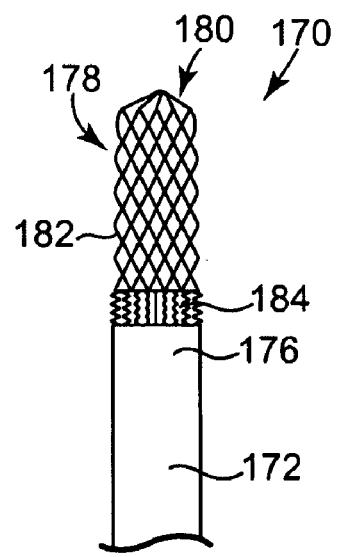
FIG. 5 is a side view of a substantially cylindrical crown disposed at a distal end of an amniotomy device according to another embodiment.

FIG. 5 is a side view of an amniotomy device 170 according to another embodiment. Amniotomy device 170 includes a shaft 172 and a crown 178 disposed on a distal end 176 of shaft 172. In one embodiment, crown 178 is generally cylindrical in shape and includes a leading bite wing surface 180, and a trailing bite wing surface 182 that is substantially orthogonal to leading bite wing surface 180. In one embodiment, a knurled surface 184 is provided at a distal end of shaft 172 adjacent to crown 178 to provide an index location for a clinician's finger when the clinician approximates the amniotic sac prior to perforating the sac.

Figure 6:
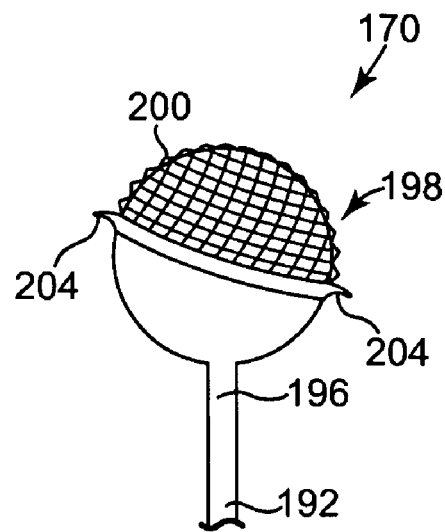
FIG. 6 is a side view of a spherically-shaped crown disposed at a distal end of an amniotomy device according to another embodiment.

FIG. 6 is a perspective view of an amniotomy device 190 according to another embodiment. Amniotomy device 190 includes a shaft 192 and a crown 198 disposed on a distal end 196 of shaft 192. Crown 198 includes a leading bite wing surface 200 configured to engage and draw amniotic sac tissue to a trailing bite wing surface 202, and trailing bite wing surface 202 is configured to rupture the amniotic sac. In one embodiment, the trailing bite wing surface 202 includes an edge 204 configured to rupture the amniotic sac without cutting cervical tissue.

Figure 7:
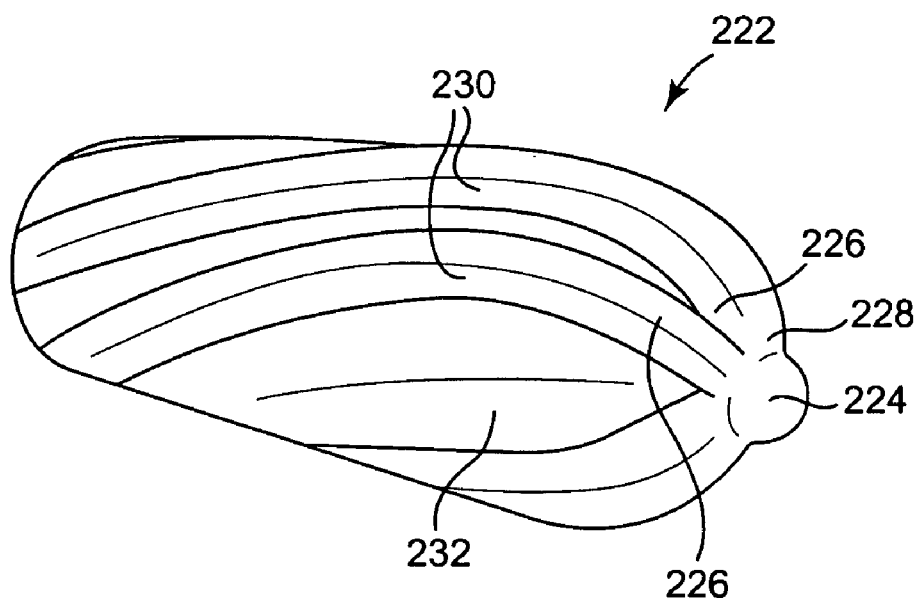
FIG. 7 is a perspective view of a clay model of an amniotomy device according to one embodiment.

FIG. 7 is a perspective view of a clay model of an amniotomy crown 222 according to one embodiment. Amniotomy crown 222 includes a blunt leading end 224, a first set of leading bite wings 226 formed on a distal surface 228 of crown 222, and a second set of trailing bite wings 230 formed on a side surface 232 of crown 222.

Figure 8:
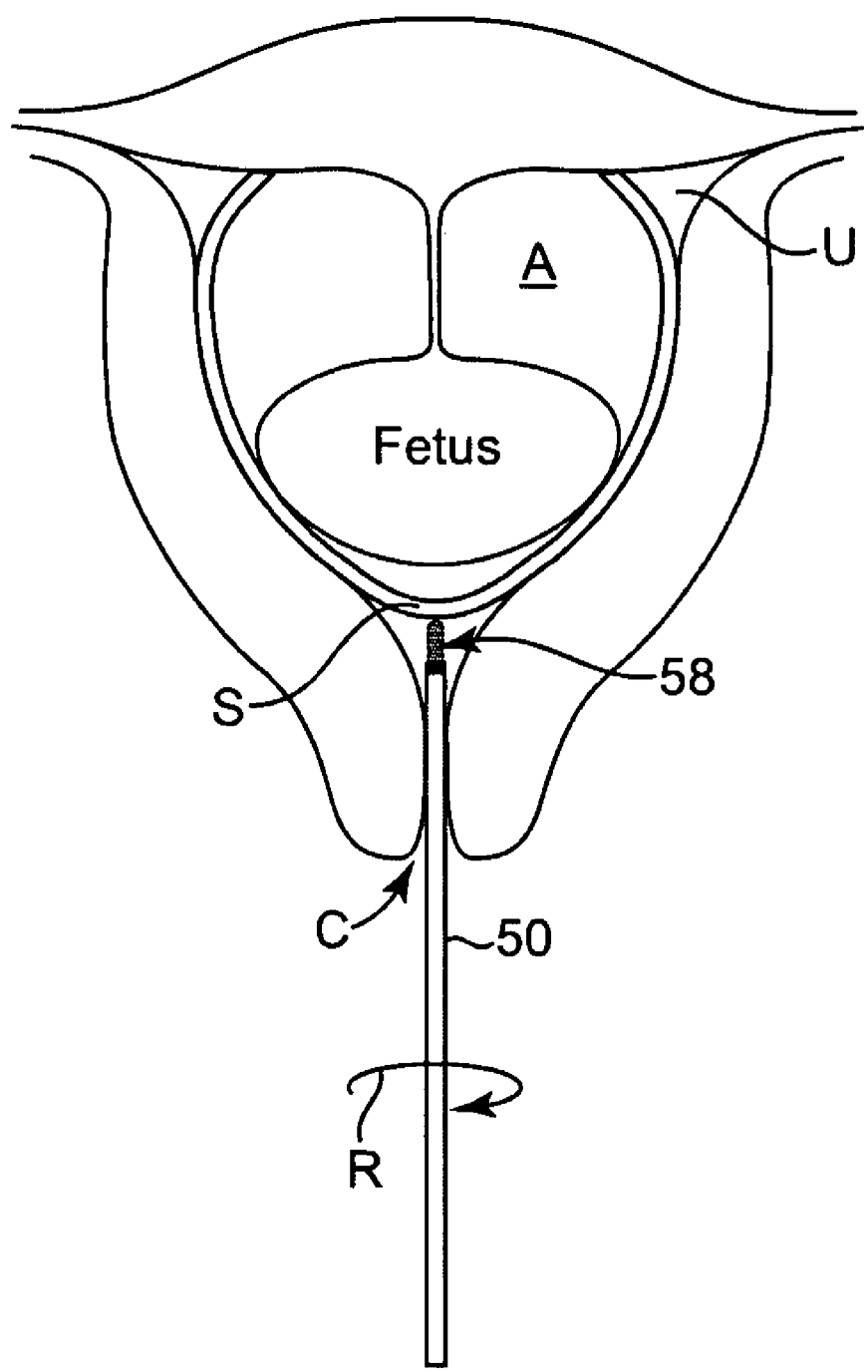
FIG. 8 is a cross-sectional illustration of a uterus containing an amniotic sac and an amniotomy device inserted through a cervix in contact with the amniotic sac according to one embodiment.

FIG. 8 is a cross-sectional illustration of a uterus U containing an amniotic sac S and an amniotomy device 50 inserted through a cervix C in contact with the amniotic sac S according to one embodiment. Amniotic sac S is disposed within uterus U and includes the amnion and chorion layers that retain the amniotic fluid A and the fetus. During pre-labor prior to the delivery of the fetus through the cervix C, a physician may determine that it is desirable to rupture the amniotic sac S to relieve the intrauterine pressure and initiate labor. To facilitate initiation of labor, the physician inserts amniotomy device 50 into the cervix C until crown 58 contacts amniotic sac S. Blunt apex 64 (FIG. 1A) at a distal end of device 50 enables the easy insertion of device 50 into the cervix C while minimizing the possibility of undesirably tearing cervical tissue. In one embodiment, blunt apex 64 is sized to enable a physician's finger to protectively cover at least a portion of the leading bite wings when inserting the rupture crown into a birth canal. That is to say, the diameter of the blunt distal end of the rupture crown is sized so that the physician is able to cover the distal end with the tip of a finger as the device is inserted into the cervix, thus minimizing the possibility of undesirably discomforting the patient. For example, the physician employs a finger to provide clearance between the cervix C and the device 50 to prevent unintentionally touching the cervix C with device 50.

By rotating amniotomy device 50 in the direction of the arrow R, leading bite wings 60 (FIG. 1A) capture the tissue of the amniotic sac S and pull a portion of the sac S down into engagement with the trailing bite wings 62, 63 (FIG. 1A). Trailing bite wings 62 or 63 rupture the amniotic sac S and release amniotic fluid A contained in the sac S, thereby inducing labor and reducing the internal pressure within the uterus U. In this manner, the physician is able to rupture the sac S membranes by sliding device 50 through the cervix C, followed by axial rotation of device 50.

Device 50 punctures the amniotic sac S via rotational motion. In contrast, the known curved devices can potentially press against the sensitive tissue of the cervix C walls as the physician moves the curved device into and out of the cervix in an attempt to engage the cutting hook or suction tube with the amniotic sac, a condition that is exacerbated when the cervical passage is relatively closed. Moreover, some known devices necessitate forcing the device axially into the cervix to hook or engage the tissue, which is a motion that could potentially unintentionally drive the device through the amniotic sac.

Other embodiments are provided below to protectively cover the cutting edges of AROM devices when inserting the device into a birth canal.

FIGS. 9A and 9B are side views of an amniotomy device 250 including a crown 258 and a sleeve 260 retractable relative to crown 258 according to one embodiment. Amniotomy device 250 includes a shaft 252 defining a proximal end 254, a distal end 256 separated from proximal end 254, crown 258 disposed on distal end 256, and a sleeve 260 that is retractable relative to crown 258. In one embodiment, shaft 252 and crown 258 are similar to shaft 52 and crown 58 described above, where crown 258 includes bite wings or other forms of a surface that is configured to engage tissue of the amniotic sac when shaft 252 is rotated. In one embodiment, sleeve 260 is configured to slide relative to crown 258 and includes a first stowed position in which crown 258 is exposed for engagement with the amniotic sac, and a second deployed, cutting position in which sleeve 260 slides over crown 258 to pierce the amniotic sac.

For example, FIG. 9A is a side view of amniotomy device 250 showing sleeve 260 retracted to the first position in which crown 258 is exposed for engagement with amniotic sac tissue. In one embodiment, about 1-2 cm of crown 258 is exposed when sleeve 260 is retracted. In other embodiments, less than 1 cm or more than 2 cm of crown 258 is exposed when sleeve 260 is retracted. In a manner consistent with that described above in FIG. 8, shaft 252, when rotated, enables crown 258 to engage and grasp the amniotic sac S tissue.

FIG. 9B is a side view of amniotomy device 250 showing sleeve 260 deployed to the second cutting position in which the sleeve 260 covers crown 258. In one embodiment, sleeve 260 includes a flange 270 disposed on a proximal end 272. Flange 270 provides a grasping surface that enables sleeve 260 to be engaged and slid distally relative to shaft 252 (upward in the orientation of FIG. 9B). In one embodiment, flange 270 is ergonomically formed to provide a pad suited for grasping by an index finger and a middle finger, for example, of a hand that engages the shaft 252. After engaging the tissue of amniotic sac S with crown 258, the clinician or physician slides sleeve 260 upward by guiding flange 270 distally with pressure from a thumb or one or more fingers. In this manner, sleeve 260 slides distally over crown 258 and a cutting surface internal to sleeve 260, described below, is configured to pierce or sever the tissue of the amniotic sac S. Stops 278 are provided to limit travel of sleeve 260. A stop 279 is provided to ensure that a cutting edge attached to sleeve 260 is not exposed when crown 258 is exposed.

Figures 10A, 10B:
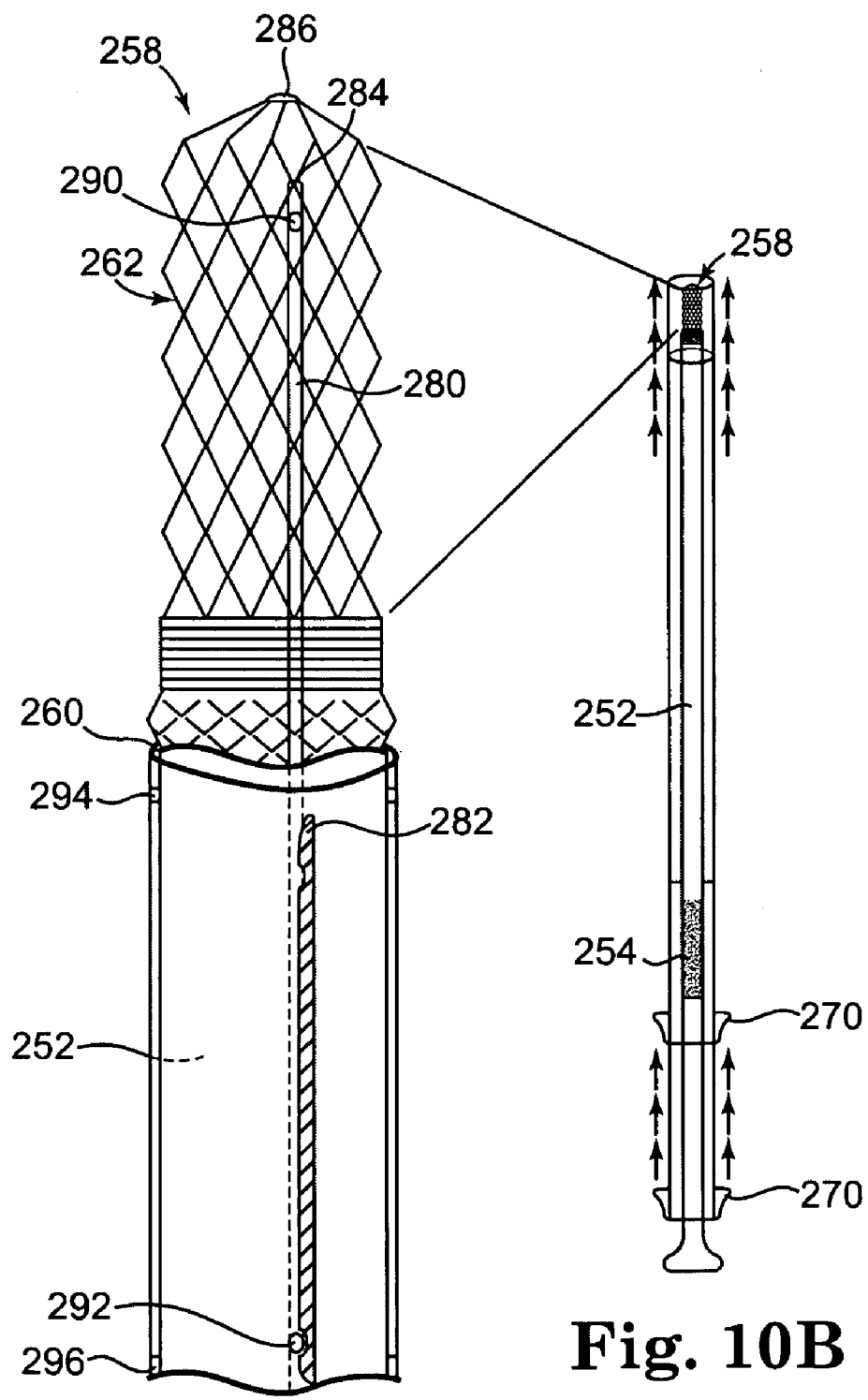
FIG. 10A is a side view of the amniotomy device shown in FIG. 9A illustrating the sleeve and a cutting edge coupled to the sleeve according to one embodiment.
FIG. 10B is a side view of the amniotomy device shown in FIG. 10A illustrating the sleeve deployed to a cutting position in which the cutting edge is protectively retained within the sleeve.

FIG. 10A is an enlarged side view of amniotomy device 250 with sleeve 260 retracted and crown 258 exposed. In one embodiment, shaft 252 defines a channel 280 and sleeve 260 includes a cutting edge 282 that is configured to slide along channel 280. In one embodiment, channel 280 extends along shaft 252 up to a point 284 that is offset from a top 286 of crown 258. In this manner, cutting edge 282 is configured to slide up channel 280 and yet not project beyond top 286 of crown 258, which protects the clinician, the mother, and the infant being delivered from cutting edge 282.

In one embodiment, channel 280 includes a first stop 290 configured to limit travel of cutting edge 282 to a point that does not project beyond the top 286 of crown 258. In one embodiment, channel 280 defines a second stop 292 configured to maintain sleeve 260 in a deployed position such that crown 258 is exposed.

In one embodiment, sleeve 260 includes an upper stop 294 and a lower stop 296. In one embodiment, stops 294, 296 include gaskets configured to seal about a perimeter of shaft 252 and crown 258 such that cover 260 encloses shaft 252 with a minimum amount of clearance.

Cutting edge 282 includes blades, hooks, serrated edges, or a sharp point configured to rupture amniotic sac tissue when cutting edge 282 is engaged with the tissue.

FIG. 10B illustrates sleeve 260 moved upward relative to crown 258 in a manner that enables cutting edge 282 to pierce or cut into tissue engaged by crown 258. Sleeve 260 includes rigid materials configured to protectively cover crown 258 and maintain cutting edge 282 within channel 280. Suitable materials for sleeve 260 include plastics and metal. In one embodiment, sleeve 260 is fabricated from stainless steel and includes cutting edge 282 integrally formed and disposed on an interior surface of sleeve 260.

FIG. 11A is a top view of crown 258. In one embodiment, shaft 252 defines a pair of opposing channels 280*a*, 280*b* formed in a side wall of shaft 252. In one embodiment, channels 280*a*, 280*b* extend to a distal end 286 of shaft 252. In another embodiment, channels 280*a*, 280*b* do not extend up to distal end 286 of shaft 252 and are offset a distance 284 away from distal end 286 (FIG. 10A).

FIG. 11B a top view of crown 258 and sleeve 260 disposed around a perimeter of crown 258. In one embodiment, sleeve 260 defines opposing cutting edges 282*a*, 282*b* that are configured to slide within opposing channels 280*a*, 280*b*, respectively.

FIGS. 12A and 12B illustrate other embodiments of cutting edges. FIG. 12A is a side view of a serrated cutting edge 298 extending from a support 299 according to one embodiment. Cutting edge 298 includes a plurality of serrations that are configured to engage with the amniotic sac S to ensure that the sac is punctured when amniotomy device 250 is employed. In one embodiment, cutting edge 298 is protectively recessed within sleeve 260 when device 250 is inserted into the vaginal introitus and is adapted to be deployed to extend from sleeve 260 in a manner configured to puncture the amniotic sac S. Support 299 is configured to properly position cutting edge 298 relative to the amniotic sac after the sac is engaged by crown 258 (FIG. 10A).

FIG. 12B is a side view of another cutting edge 300 according to one embodiment. Cutting edge 300 includes a support 302. Support 302 is configured to engage with stop 290 (FIG. 10A) such that cutting edge 300 is exposed relative to crown 258 (FIG. 10A). In this manner, after the amniotic sac S is engaged by crown 258, cutting edge 300 is properly positioned to puncture the sac.

Figure 13:
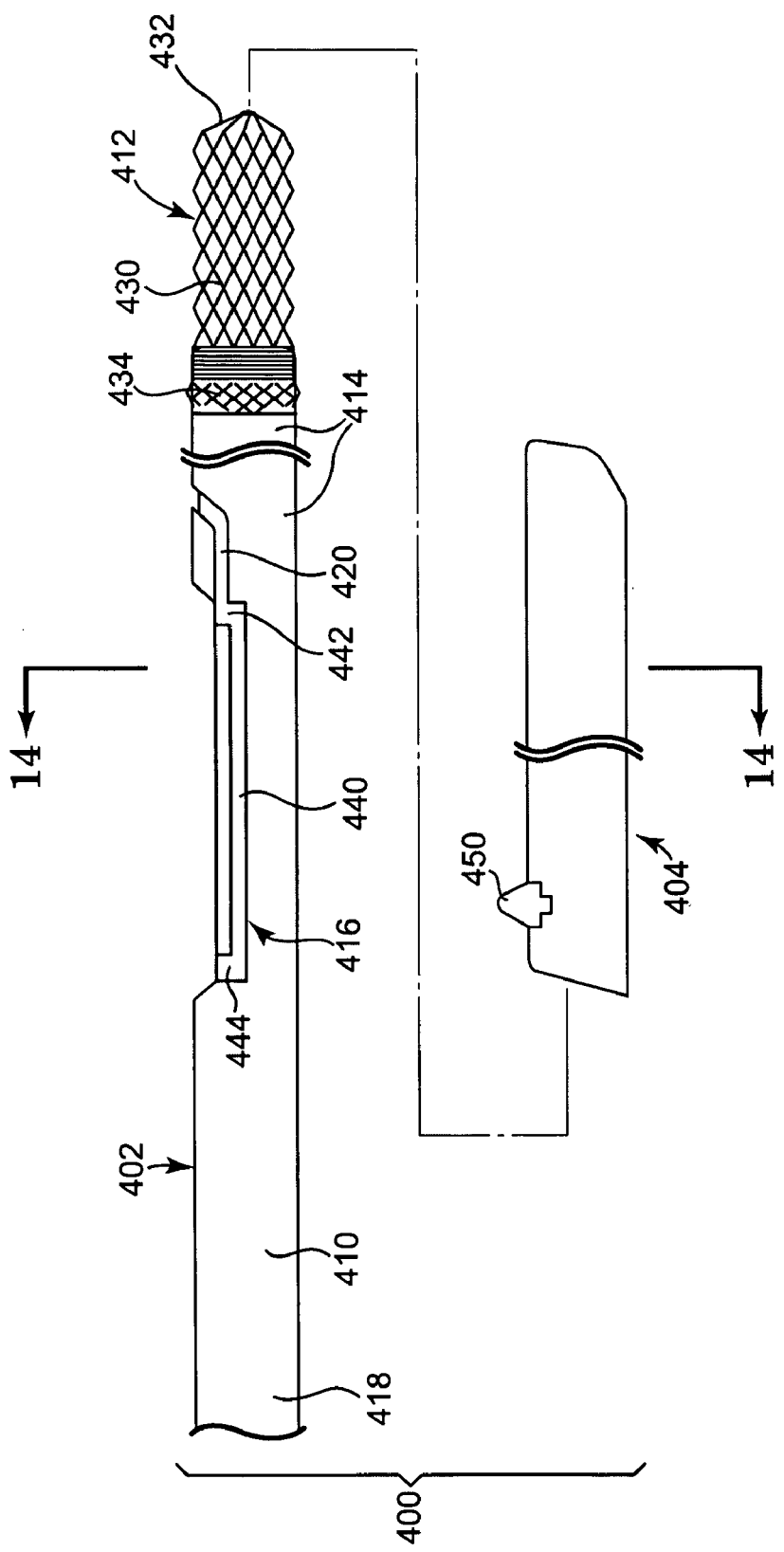
FIG. 13 is an exploded side view of a protective sleeve that is configured to be slideably coupled to an amniotomy assembly according to one embodiment.

FIG. 13 is a partially exploded side view of an amniotomy assembly 400 according to one embodiment. Amniotomy assembly 400 includes an amniotomy device 402 and a protective tubular sleeve 404 that is attachable to amniotomy device 402. In one embodiment, tubular sleeve 404 is removable from amniotomy device 402 to enable cleaning of device 402 and disposal/replacement of sleeve 404. In general, tubular sleeve 404 slides along a distal portion of amniotomy device 402 to selectively expose a cutting head provided on a distal end of amniotomy device 402.

In one embodiment, amniotomy device 402 includes a shaft 410, a rupture crown 412 disposed at a distal end portion 414 of shaft 410, a channel 416 formed in shaft 410 to extend between distal end portion 414 and a mid-region 418 of shaft 410, and a relief slot 420 communicating with channel 416.

In one embodiment, rupture crown 412 is similar to crown 58 (FIG. 1B) and includes a first set 430 of leading bite wings formed adjacent a distal end 432 of shaft 410 and a second set 434 of trailing bite wings formed on a side of rupture crown 412 along a side of shaft 410 and adjacent to distal end portion 414. Amniotomy device 402 as described above is rotatable such that first set 430 of leading bite wings engage with amniotic sac. Further rotation of shaft 410 transports tissue of the amniotic sac to the second set 434 of trailing bite wings, which are configured to rupture the amniotic sac.

Channel 416 extends along a portion of shaft 410. In one embodiment, channel 416 includes a longitudinal channel 440 that is parallel to a longitudinal axis of shaft 410, a distal section 442 communicating with longitudinal channel 440, and a proximal section 444 also communicating with longitudinal channel 440. Channel 416 is formed in shaft 410 by a suitable process such as milling, molding, or other process configured to form a relief in shaft 410. In one embodiment, distal section 442 and proximal section 444 are formed to be substantially normal to the longitudinal axis of shaft 410 (and normal to longitudinal channel 440).

Tubular sleeve 404 is configured to be introduced over distal end 432 of shaft 410 and slid along relief slot 420 until engaged with channel 416. When so assembled, tubular sleeve 404 is moveable relative to rupture crown 412 between a first position in which rupture crown 412 is protected and resides within tubular sleeve 404 and a second position in which rupture crown 412 extends out of tubular sleeve 404. A plunger 450 is provided that deflects (e.g., up and down) to guide a structure formed inside of tubular sleeve 404 between distal section 442, longitudinal channel 440, and proximal section 444 of channel 416 as tubular sleeve 404 moves along shaft 410.

Shaft 410 has a length of between about 14-16 cm. It is to be understood that tubular sleeve 404 retracts back onto mid-region 418 of shaft 410 in a manner that fully exposes rupture crown 412, such that rupture crown 412 is able to access the vagina without interference by tubular sleeve 404.

Figure 14:
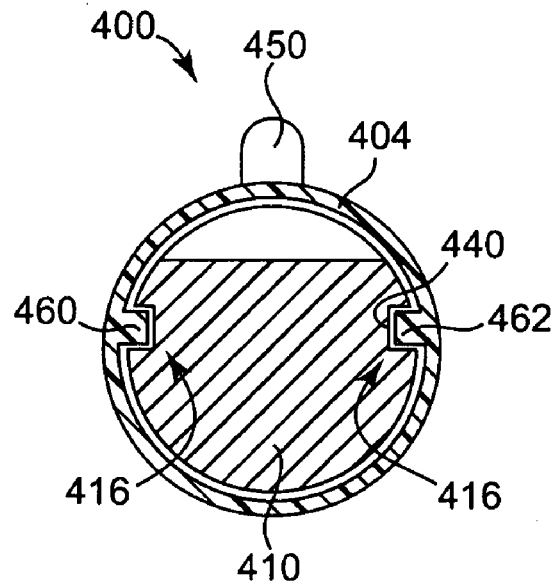
FIG. 14 is a cross-sectional view of the protective sleeve coupled to a shaft of the amniotomy assembly shown in FIG. 13.

FIG. 14 is a cross-sectional view of amniotomy assembly 400 illustrating tubular sleeve 404 engaged with opposing channels 416 formed in longitudinal channel 440. In one embodiment, tubular sleeve 404 includes a first boss 460 engaged with a first one of channels 416 and a second boss 462 engaged with the opposing channel 416. Bosses 460, 462 are configured to ride within channel 416 to enable tubular sleeve 404 to move within channels 416. In one embodiment, tubular sleeve 404 is disposed over less than half of a length of shaft 410 and is configured such that when bosses 460, 462 are engaged in proximal section 444 of channel 416, rupture crown 412 is exposed relative to tubular sleeve 404. When bosses 460, 462 are engaged in distal section 442 of channel 416, tubular sleeve 404 protectively shrouds or covers rupture crown 412.

In one embodiment, bosses 460, 462 communicate with plunger 450. When plunger 450 is retracted rearward with a thumb, bosses 460, 462 moves into proximal section 444 and tubular sleeve 404 is selectively retained (or locked) in the second rupture position. When plunger 450 is depressed and pushed forward, bosses 460, 462 are directed out of proximal section 444 into longitudinal section 440, thus moving tubular sleeve 404 over rupture crown 412.

Figure 15:
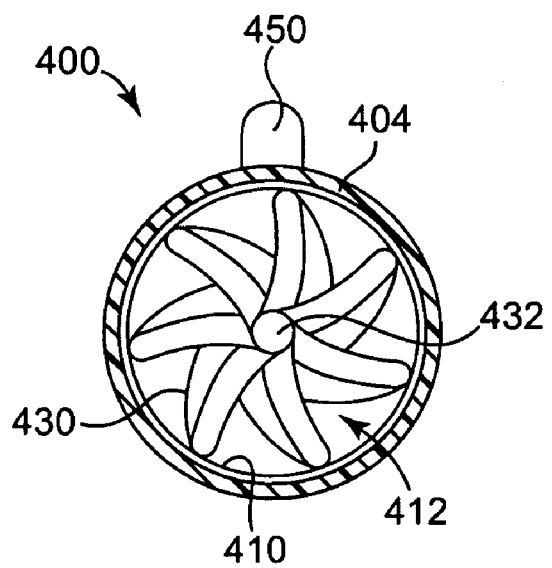
FIG. 15 is a front view of the protective sleeve attached to the amniotomy assembly shown in FIG. 13.

FIG. 15 is a front view of distal end 432 of amniotomy assembly 400. Tubular sleeve 404 is disposed in close proximity around shaft 410 and moveable to selectively expose bite wings 430.

FIG. 16A is a cross-sectional view of an amniotomy assembly 500 according to another embodiment. Amniotomy assembly 500 includes an amniotomy device 502 axially disposed within a protective tubular sleeve 504 and an advancer 506 coupled to amniotomy device 502. A portion of advancer 506 is inserted within tubular sleeve 504 and a second portion of advancer 506 is exposed outside of tubular sleeve 504 and configured to be manipulated in presenting the cutting end portion of amniotomy device 502 into and out of tubular sleeve 504.

Amniotomy device 502 is similar to those devices described above and includes a rupture crown 510 having a first set 512 of leading bite wings formed on a distal end of rupture crown 510 and a second set 514 of trailing bite wings formed on a side of rupture crown adjacent to a distal end portion 516 of shaft 518. Advancer 506 is coupled to shaft 518 on a proximal end 520 opposite rupture crown 510.

In one embodiment, advancer 506 is provided as a part of shaft 518 and includes a U-shaped advancer having a first leg 530 that is co-linear with shaft 518, a second leg 532 parallel to first leg 530, and a base 534 connected between proximal ends of first and second legs 530, 532. In one embodiment, first leg 530 includes a leading bead 536 and a trailing bead 538, both of which project toward second leg 532, and a stopper 540 that projects away from second leg 532. First and second beads 536, 538 are provided to selectively position or "lock" amniotomy device 502 relative to sleeve 504 as device 502 is moved between a first position in which rupture crown 510 extends from tubular sleeve 504 and a second position in which rupture crown 510 is protectively stowed inside tubular sleeve 504. Stopper 540 is provided to limit axial travel of U-shaped advancer 506 as first leg 530 moves within sleeve 504.

In one embodiment, protective sleeve 504 includes an external finger hold 540 that enables one-handed use of amniotomy assembly 500 by a physician during an AROM procedure and pincers 542 that assist trailing bite wings 514 in rupturing the amniotic membranes. Pincers 542 are disposed within sleeve 504 and configured to contact a portion of rupture crown 510 to ensure that tissue entrained by crown 510 is sheared (i.e., ruptured) when crown 510 is retracted into sleeve 504.

FIG. 16B is a cross-sectional view of amniotomy device 502 protectively stowed within tubular sleeve 504. Advancer 506 has been retracted and trailing bead 538 projects from a window formed in sleeve 504 to retain device 502 in the stowed position. Leading bead 536 is depressed against an interior surface of tubular sleeve 504. In this manner, the sharp bite wings 512, 514 are protectively encased within tubular sleeve 504 and configured for the safe insertion of assembly 500 into the cervix for an AORM procedure.

After insertion of assembly 500 and immediately prior to membrane rupture, second leg 532 is depressed against trailing bead 538, which presses bead 538 into window and enables advancer 506 to move forward to expose rupture crown 510 beyond sleeve 504 (See FIG. 16A). To initiate membrane rupture, assembly 500 is rotated to engage bite wings 512, 514 with amniotic sac. Retraction of amniotomy device 502 into sleeve 504 draws the amniotic sac across pincers 542 inside a distal end of sleeve 504. Pincers 542 combine with bite wings 512, 514 to ensure that amniotic sac is severed during the AORM procedure.

FIG. 17 is a top view of tubular sleeve 504. Tubular sleeve 504 defines an opening 570 sized to receive leading bead 536 (FIG. 16A), a window 572 adjacent to proximal end 574, and an intermediate window 576 formed between opening 570 and first window 572. With reference to FIG. 16A, when advancer 506 is directed into tubular sleeve 504, leading bead 536 projects through opening 570 and trailing bead 538 projects through intermediate window 576. In this manner, beads 536, 538 "lock" advancer 506 relative to sleeve 504 such that rupture crown 510 is exposed in a cutting or AROM position.

With reference to FIG. 16B, when advancer 506 is retracted, trailing bead 538 is drawn into first window 572 and leading bead 536 is retained inside tubular sleeve 504 between opening 570 and intermediate window 576. In this manner, trailing bead 538 selectively locks into window 572 to retain amniotomy device 502 in the stowed, protected position. Other configurations for selectively locking or retaining device 502 relative to sleeve 504 are also acceptable.

FIG. 18 is a bottom view of tubular sleeve 504. A slot 580 is formed adjacent to proximal end 574 and sized to receive stopper 540 (FIG. 16A). Stopper 540 slides within slot 580 between a leading edge 582 that limits forward travel of advancer 506 and a trailing edge 584 that limits rearward travel of advancer 506.

In one embodiment, protective sleeve 504 presents a substantially circular transverse cross-sectional shape, although other shapes are also acceptable. Assembly 500 is suited for one-handed use in first inserting assembly 500 into the vagina adjacent to the cervix and thereafter advancing rupture crown 510 from sleeve 504 by manipulating advancer 506 with a thumb. Circular cross-sectional shape of protective sleeve 504 enables assembly 500 to be comfortably rotated to engage amniotic sac with rupture crown 510. Thereafter, the physician places an index finger proximal to finger hold 550 and retracts advancer 506 with the thumb (or other fingers) to rupture the amniotic membranes.

During use, the amniotomy devices provided herein are configured to access a relatively closed endocervical canal and rupture an amniotic sac in an atraumatic manner that minimizes the force applied to the adjacent vaginal walls. In contrast, the known amniotomy devices necessitate "hooking" or engagement of the amniotic sac by directing the device against the vaginal walls, and prying the device further into the vaginal walls to rupture the amniotic membrane.

The amniotomy devices described herein provide for direct and atraumatic access into the relatively closed cervical canal when approximating the amniotic sac. Rotation of the amniotomy device in a first direction, clockwise for example, engages the tissue of the amniotic sac and draws the tissue in contact with a trailing bite wing surface. Upward movement of a sleeve coupled to a shaft of the amniotomy device directs a cutting edge protectively recessed within the sleeve into contact with the amniotic sac, thus rupturing the membrane without uncomfortable and undesirable lateral force applied to the adjacent vaginal walls.

Embodiments described above provide an amniotomy device configured to access a relatively closed endocervical canal and rupture an amniotic sac in an atraumatic manner relative to the adjacent tissue. The amniotomy devices described above provide for direct access into the relatively closed cervical canal when approximating the amniotic sac. Rotation of the amniotomy device in a first direction, clockwise for example, engages the tissue of the amniotic sac and draws the tissue in contact with a trailing bite wing surface. Additional rotation of the shaft ruptures the amniotic sac. Rotating the amniotomy devices in a second direction, counter-clockwise for example, results in the crown of the amniotomy device smoothly turning in contact with the amniotic sac and not engaging the tissue of the amniotic sac. In this regard, the amniotomy devices described above are configured to selectively engage with the tissue of the amniotic sac to enable the controlled and selective rupturing of the tissue membranes via rotation of the shaft.

Embodiments described above provide an amniotomy device configured to access a relatively closed endocervical canal and rupture an amniotic sac in an atraumatic manner relative to the adjacent tissue. The amniotomy devices provide for direct access into the relatively closed cervical canal when approximating the amniotic sac. Rotation of the amniotomy device in a first direction, clockwise for example, engages the tissue of the amniotic sac and draws the tissue in contact with a trailing bite wing surface. Upward movement of a sleeve coupled to a shaft of the amniotomy device directs a cutting edge protectively recessed within the sleeve into contact with the amniotic sac, thus rupturing the membrane.

It is to be understood that the features of the various exemplary embodiments described herein may be combined with each other, unless specifically noted otherwise.

By convention, "end" means the endmost location (the very end) of an object, and "end portion" means a segment length extending a distance away from the end of the object. Thus, "distal end" means the very end of an object that is directed away from a user of the object, and "proximal end" means the very end of an object that is nearest the user of the object.

FIGS. 19-24 are perspective views of various embodiments of rupture crowns of amniotomy devices.

Figure 19A:
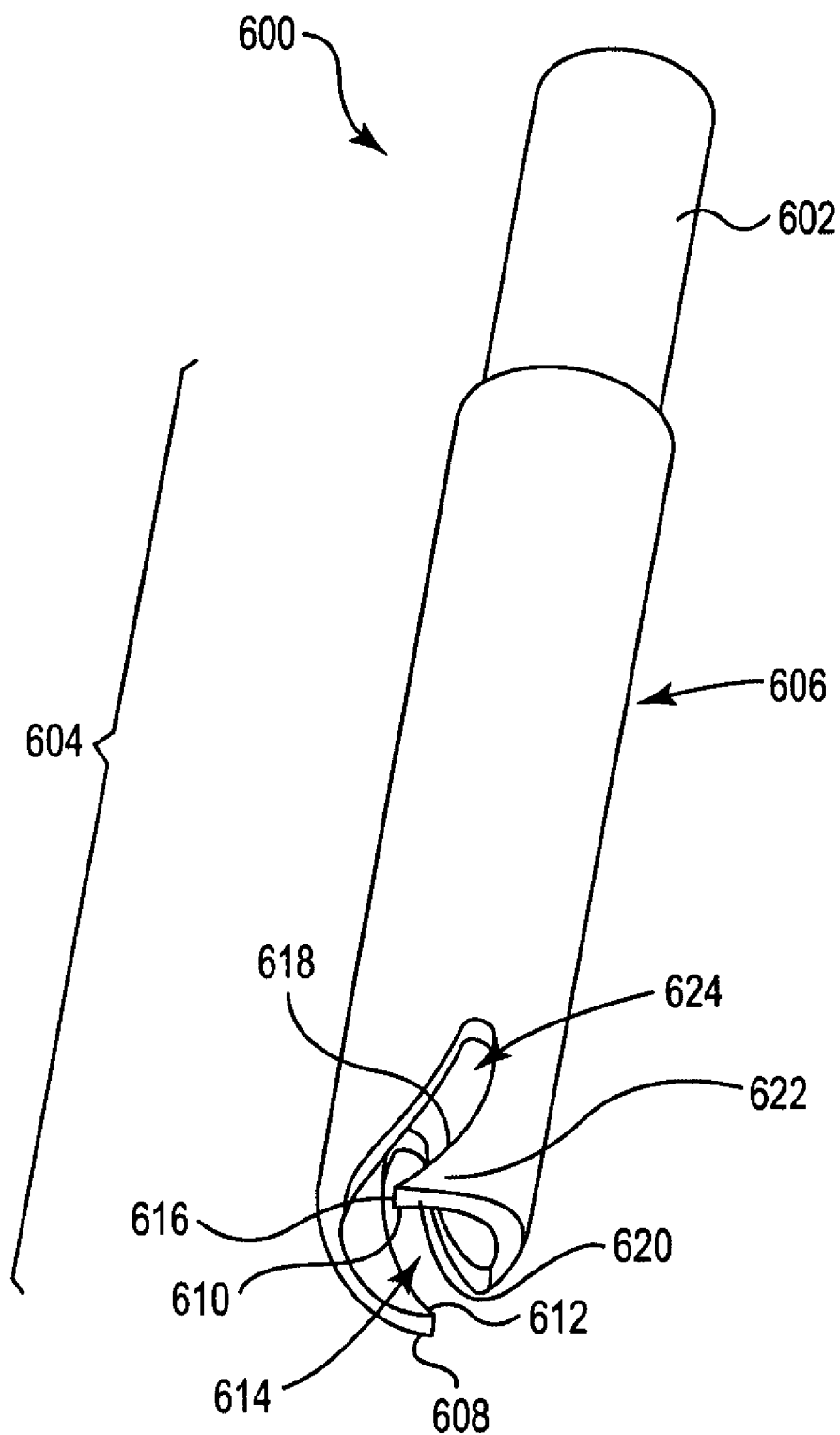
FIGS. 19A-24 are perspective views of various embodiments of rupture crowns of amniotomy devices.

FIG. 19A is a perspective view of an amniotomy device 600 according to one embodiment. Amniotomy device 600 includes a shaft 602 (only a portion of which is illustrated) having a distal end portion 604 and a rupture crown 606 disposed along distal end portion 604. In one embodiment, rupture crown 606 includes a distal end 608 defined by a first leading bite wing 610 and a second leading bite wing 612 and has a recess 614 formed in distal end 608 between bite wings 610, 612. The leading bite wings 610, 612 are configured to engage amniotic membrane when shaft 602 is rotated and rupture the amniotic membrane.

Shaft 602 is similar to shaft 252 (FIGS. 10A and 10B) described above and is suitable for disposing within a sleeve such as sleeve 260 (FIG. 10A). In one embodiment, shaft 602 and rupture crown 606 have substantially the same diameter. Alternatively, shaft 602 has a diameter that is smaller than a diameter of rupture crown 606, in which case rupture crown 606 extends over a footprint of shaft 602.

In one embodiment, rupture crown 606 is formed as a circular cylinder such that a lateral cross-section of rupture crown 606 provides a substantially circular perimeter. In one embodiment, bite wing 610 terminates at a pointed edge 616 that is formed as a cusp-like cutting shape between surface 618 and surface 620. Pointed edge 616 is formed within a periphery of the circular rupture crown 606 such that the outermost surface of rupture crown 606 is defined by exterior surface 622 of bite wing 610. Consequently, pointed edge 616 of bite wing 610 is exposed on distal end 608 and does not extend beyond exterior surface 622, which configures rupture crown 606 to effectively engage with the amniotic sac while minimizing the likelihood of tissue discomfort when inserting amniotomy device 600 into cervix C (FIG. 8).

In one embodiment, bite wings 610, 612 are provided as pointed projections that extend around distal end 608 of rupture crown 606 in a circular arc. In other words, bite wings 610, 612 have a circular boundary provided by exterior surface 622 of rupture crown 606. Recess 614 is an annular recess formed in distal end 608 to extend a distance into distal end portion 604 of rupture crown 606. In one embodiment, surface 618 is formed by opening a slot 624 into exterior surface 622 of rupture crown 606, such that slot 624 communicates with annular recess 614.

When amniotomy device 600 is employed to rupture an amniotic sac, rupture crown 606 is introduced into the cervix C (FIG. 8) into contact with amniotic sac S, shaft 602 is rotated, and opposing bite wings 610, 612 grasp the amniotic membrane. Recess 614 provides clearance to receive the amniotic membrane that is wrapped onto and over rupture crown 606. The amniotic sac may be ruptured by a slight tug delivered to amniotomy device 600 or by further rotating amniotomy device 600 by twisting shaft 602.

Figure 19B:
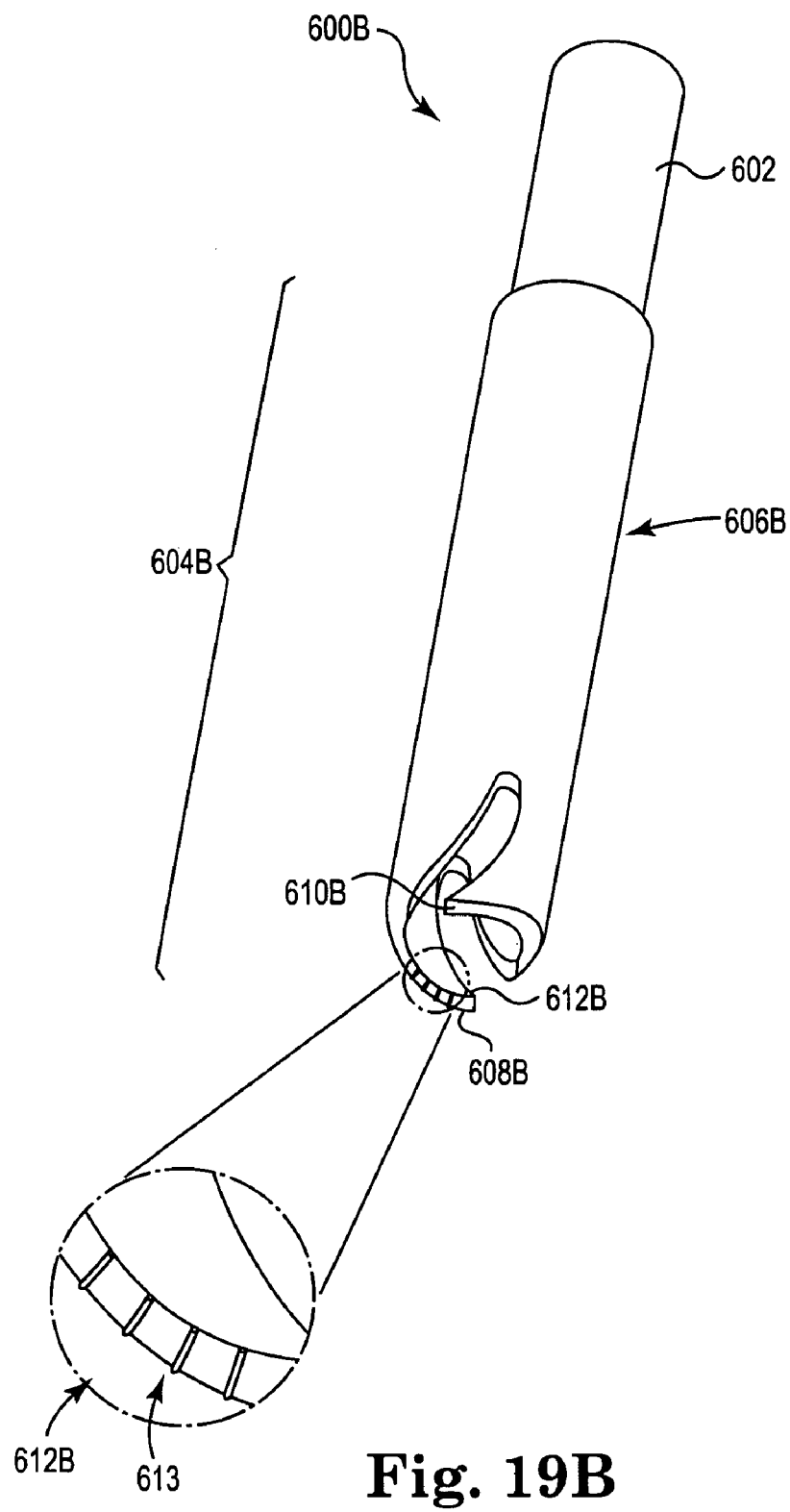

FIG. 19B is a perspective view of another embodiment of an amniotomy device 600B. Amniotomy device 600B is similar to device 600 (FIG. 19A) and includes a distal end portion 604B provided with and a rupture crown 606B. In one embodiment, rupture crown 606B includes a distal end 608B defined by a first leading bite wing 610B and a second leading bite wing 612B, where one or both of the leading bite wings 610B, 612B are formed to include a serrated leading edge defined by multiple smaller bite wings 613 or bite teeth 613. Bite wings 610, 612 and bite teeth 613 combine to engage amniotic membrane when shaft 602. The positive engagement of the amniotic sac by the multiplicity of leading-end bite wings results in consistent and controlled rupture of the amniotic membrane.

Figure 20:
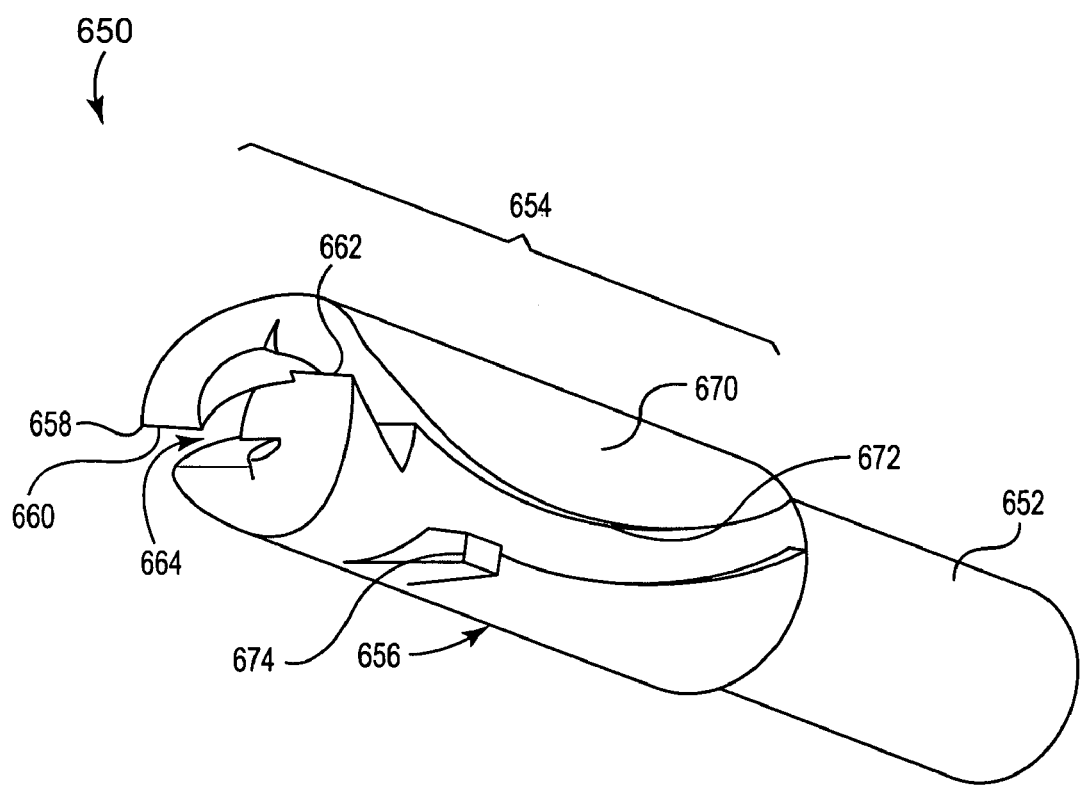

FIG. 20 is a perspective view of another embodiment of an amniotomy device 650. Amniotomy device 650 includes a shaft 652 providing a distal end portion 654, and a rupture crown 656 disposed along distal end portion 654 and defining a distal end 658. In one embodiment, distal end 658 of rupture crown 656 is defined by a first leading bite wing 660 and a second leading bite wing 662 disposed on an opposing side of a recess 664 formed in distal end 658 of rupture crown 656.

In one embodiment, a lateral cross-section of rupture crown 656 is substantially circular, although embodiments of rupture crown 656 can include a conical shape. An exterior surface 670 of rupture crown 656 is formed to include one or more trailing bite wings 672 and/or 674 configured to wrap amniotic membrane onto the rupture crown. For example, in one embodiment exterior surface 670 is formed to include a groove 672 that provides a trailing bite wing configured to grasp and engage with amniotic membrane that is pulled down over rupture crown 656. In one embodiment, groove 672 is a helical groove and is configured to auger or engage amniotic membrane when shaft 652 is rotated. In one embodiment, the trailing bite wing of rupture crown 656 is provided as a prong 674 that projects from exterior surface 670. Prong 674 is configured to capture amniotic membrane as shaft 652 is rotated, and further provides a mechanism for tearing the amniotic membrane when shaft 652 is pulled or rotated.

It is to be understood that one or both of bite wings 660, 662 could be modified to include a multiplicity of smaller leading bite wing teeth, similar to teeth 613 illustrated in FIG. 19B.

Figure 21:
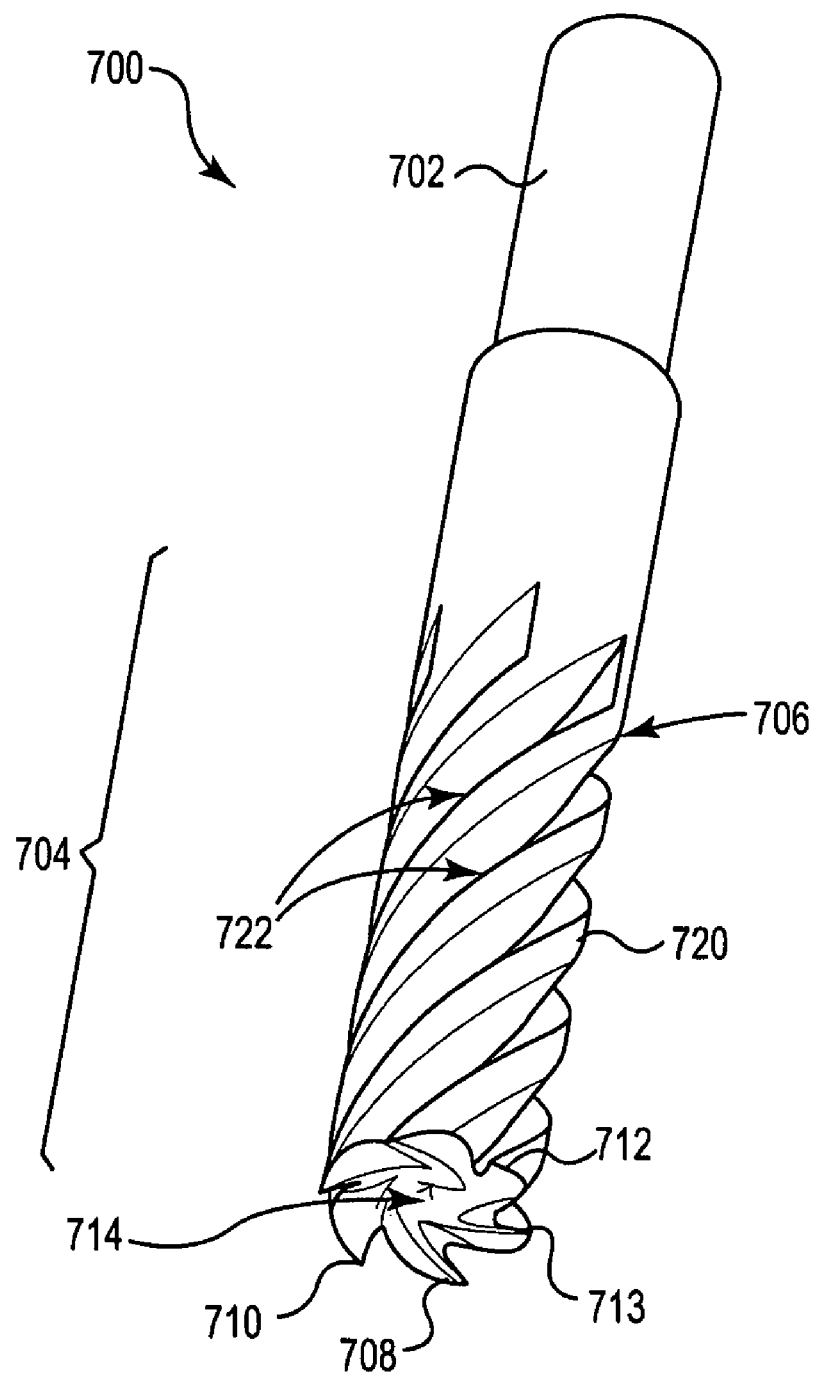

FIG. 21 is a perspective view of another embodiment of an amniotomy device 700. Amniotomy device 700 includes a shaft 702 providing a distal end portion 704 and a rupture crown 706 disposed along distal end portion 704. Rupture crown 706 includes a distal end 708 defined by multiple leading bite wings 710, 712, 713 disposed around a recess 714 formed in distal end 708. In one embodiment, recess 714 is formed as a semi-spherical depression in distal end 708.

In one embodiment, a lateral cross-section of rupture crown 706 is generally circular, and each of the leading bite wings 710, 712, 713 curve around an exterior surface of rupture crown 706 such that a portion of each bite wing is formed in a circular arc.

In one embodiment, an exterior surface 720 of rupture crown 706 is fabricated to include trailing bite wings 722. For example, in one embodiment exterior surface 720 is fabricated to include multiple grooves 722 that extend along a portion of the length of distal end portion 704 to provide trailing bite wings configured to engage amniotic membrane as shaft 702 is rotated.

Each of the leading bite wings 710, 712, 713 terminate in a point that is disposed at distal end 708 of rupture crown 706. The points are configured to minimize discomfort to the patient since the bite wings 710, 712, 713 fall along a circular arc on the perimeter of the rupture crown 706 in a manner that prevents the points from projecting beyond crown 706. When rupture crown 706 is rotated by rotating shaft 702, bite wings 710, 712, 713 entrain or dig into the amniotic membrane and pull it over rupture crown 706. Subsequent twisting of shaft 702 augers the amniotic membrane over rupture crown 706 where trailing bite wings 722 further engage with the amniotic membrane. In this manner, rotating shaft 702 twists the amniotic membrane over rupture crown 706 to facilitate a controlled rupturing of the amniotic sac.

Figure 22:
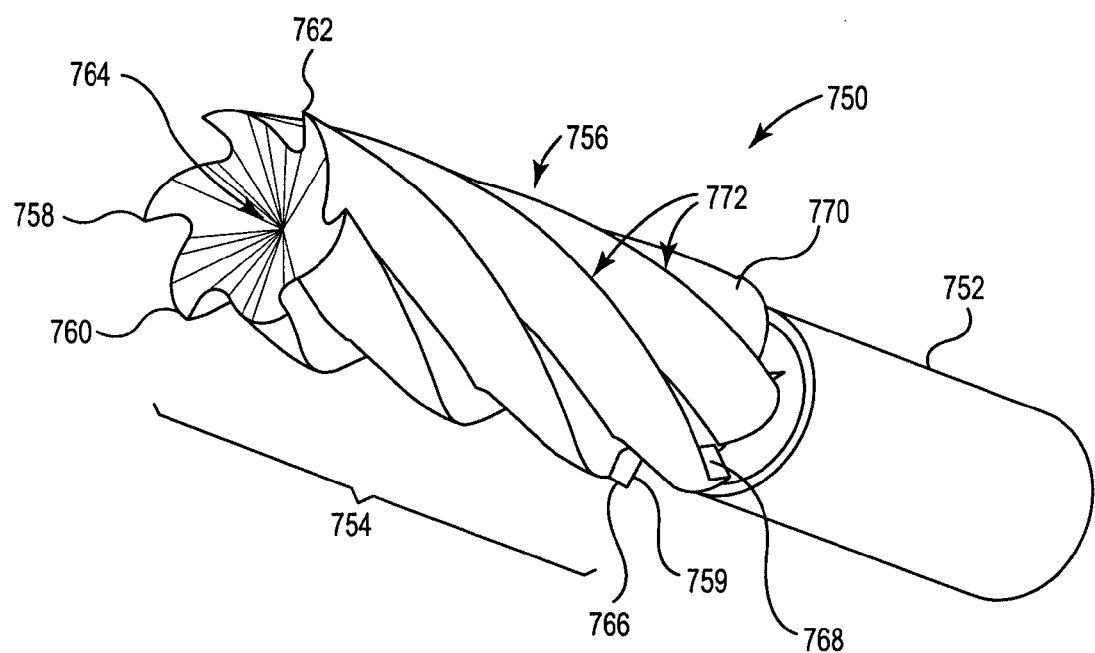

FIG. 22 is a perspective view of another embodiment of an amniotomy device 750. Amniotomy device 750 includes a shaft 752 providing a distal end portion 754 and a rupture crown 756 formed along distal end portion 754 between a distal end 758 and a proximal end 759. In one embodiment, distal end 758 is defined by leading bite wings 760, 762 that are formed on a periphery of a recess 764. Recess 764 is formed in distal end 758. Proximal end 759 of rupture crown 756 is defined by a plurality of trailing bite wings 766, 768. Rupture crown 756 thus includes leading bite wings 760, 762 formed at distal end 758 and trailing bite wings 766, 768 formed at proximal end 759.

In on embodiment, a lateral cross-section of rupture crown 756 is circular and exterior surface 770 tapers between distal end 758 and proximal end 759. Each leading bite wing 760, 762 is formed along an arc on an exterior surface 770 of rupture crown 756. The bite wings 760, 762 are thus protectively "tucked inside" a periphery of the circular exterior of rupture crown 756. In one embodiment, grooves 772 are formed between distal end 758 and proximal end 759, where the grooves 772 and the bite wings 760, 762, 766, 768 combine to grasp and positively engage amniotic membrane when shaft 752 is rotated.

Figure 23:
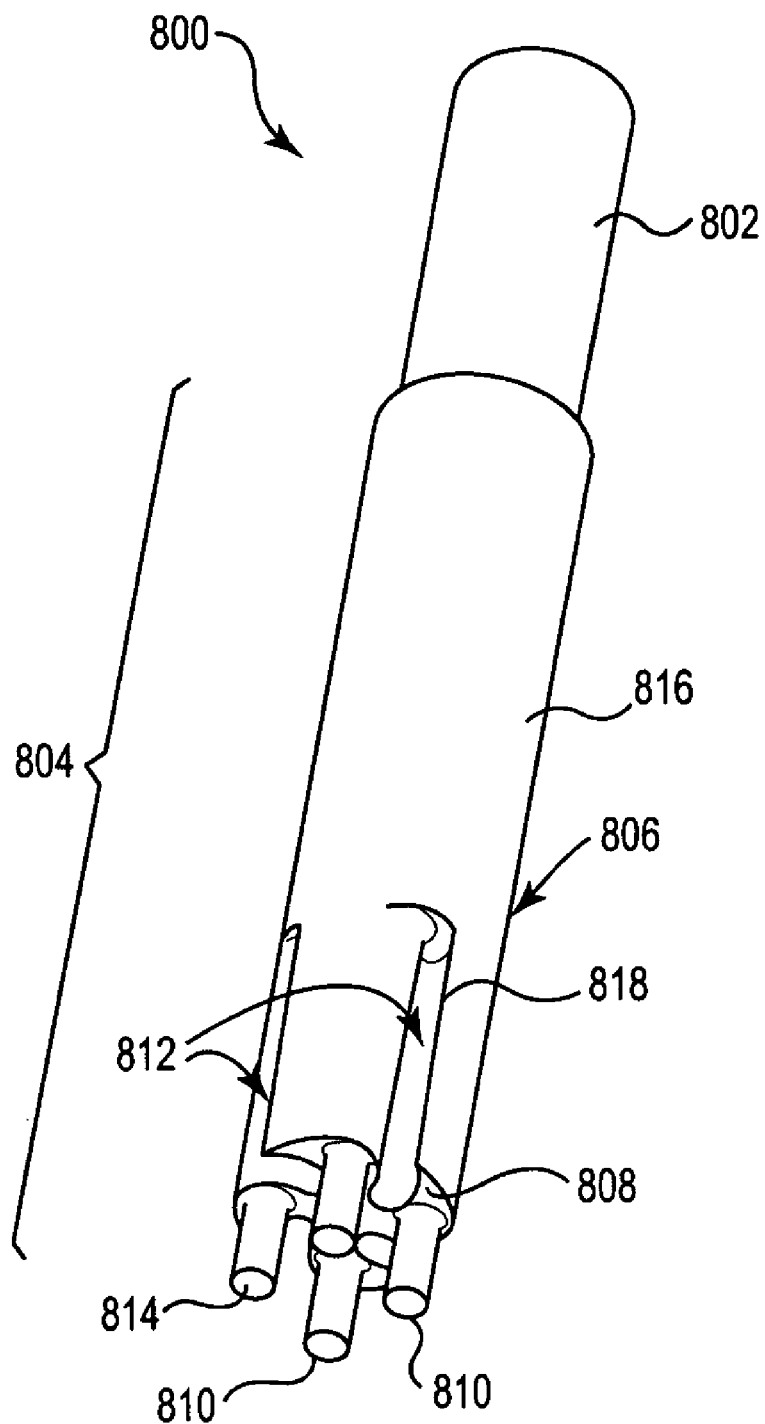

FIG. 23 is a perspective view of another embodiment of an amniotomy device 800. Amniotomy device 800 includes a shaft 802 having a distal end portion 804 and a rupture crown 806 disposed along distal end portion 804. In one embodiment, rupture crown 806 includes a distal face 808, multiple prongs 810 extending axially relative to shaft 802 from distal face 808, and multiple axial recesses 812 formed in distal face 808. Prongs 810 are generally disposed between adjacent axial recesses 812 and extend from distal face 808 to define a distal end 814 of rupture crown 806. In one embodiment, axial recesses 812 are formed in an exterior surface 816 of rupture crown 806 and extend from distal face 808 along a portion of distal end portion 804. In this manner, an exposed edge 818 is formed relative to each of the axial recesses 812, and the edges 818 provide a trailing bite wing configured to engage amniotic membrane.

While four prongs 810 and four axial recesses 812 are illustrated, it is to be understood that a different number (more or less) of prongs and recesses could be formed on rupture crown 806.

When shaft 802 is rotated, prongs 810 grasp amniotic membrane and draw the amniotic membrane between prongs 810 and into recesses 812. This positive engagement of rupture crown 806 with amniotic membrane provides the attending physician improved control in rupturing the amniotic sac when compared to conventional amniotic rupturing devices.

Figure 24:
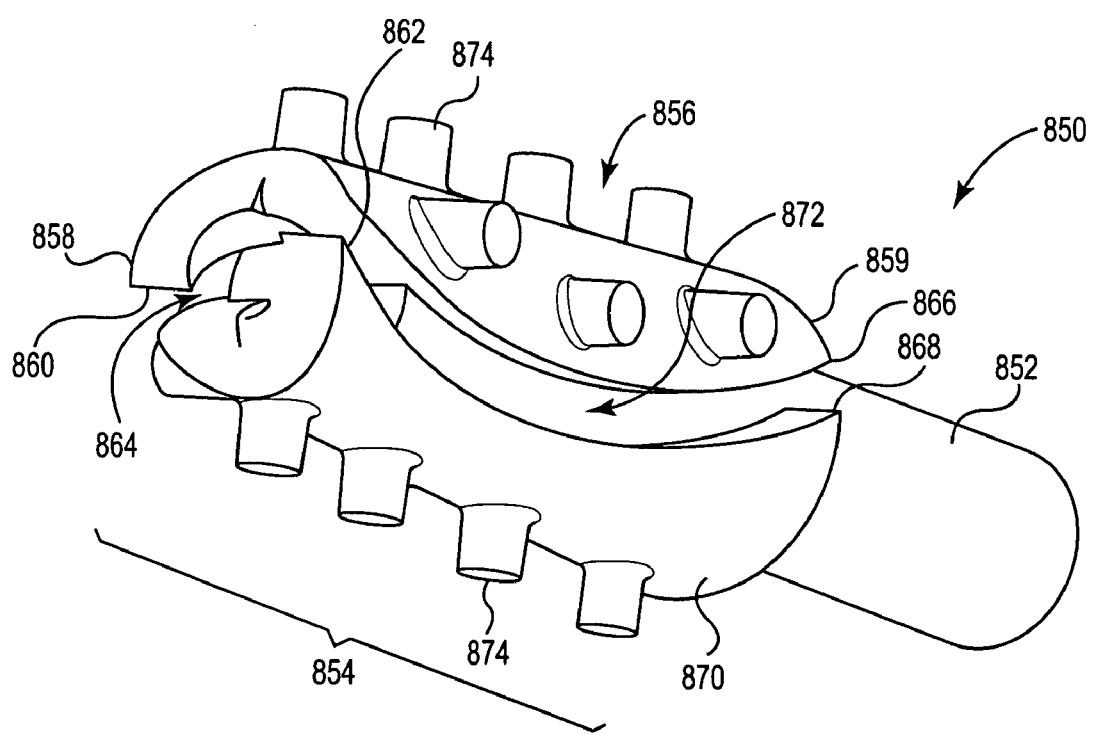

FIG. 24 is a perspective view of another embodiment of an amniotomy device 850. Amniotomy device 850 includes a shaft 852 that provides a distal end portion 854 and a rupture crown 856 disposed along distal end portion 854. Rupture crown 856 extends between a distal end 858 and a proximal end 859. Leading bite wings 860, 862 are formed on distal end 858 around a periphery of a recess 864 formed in distal end 858. In one embodiment, proximal end 859 is defined by trailing bite wings 866, 868.

In one embodiment, an exterior surface 870 of rupture crown 856 defines a circle in lateral cross-section and includes one or more grooves 872 formed and extending between distal end 858 and proximal end 859. Exterior surface 870 generally tapers between distal end 858 and proximal end 859, although non-tapered (e.g., cylindrical) forms of exterior surface 870 are also acceptable. In on embodiment, groove 872 is an auger-style or helical-style groove configured to capture and/or engage with amniotic membrane of an amniotic sac.

In one embodiment, multiple prongs 874 are formed to extend from exterior surface 870 of rupture crown 856. In one embodiment, prongs 874 extend normal from exterior surface 870 and include a first set of prongs disposed in a column on a first side of groove 872 and a second set of prongs disposed in a column on a second side of groove 872. It is desirable to stagger the first set of prongs relative to the second set of prongs to ensure that the amniotic membrane captured by rupture crown 856 is securely grasped, which prevents the amniotic membrane from undesirably disengaging with rupture crown 856.

It is to be understood that one or both of bite wings 860, 862 could be modified to include a multiplicity of smaller leading bite wing teeth, similar to teeth 613 illustrated in FIG. 19B.

In one embodiment, the length of the distal end portion of the above-described amniotomy devices illustrated in FIGS. 19-24 is between approximately 0.75-2 inches, and preferably the length of the distal end portion of the amniotomy devices is between about 1-1.5 inches. The diameter of the rupture crown of the amniotomy devices illustrated in FIGS. 19-24 is between approximately 2-10 millimeters, and preferably the diameter of the rupture crowns of the amniotomy devices is between about 3-6 millimeters.

In one embodiment, the above-described amniotomy devices illustrated in FIGS. 19-24 are formed from a polymer, for example in a molding process or an extrusion process or other suitable plastic forming process. Suitable polymers include polyolefin, polyamide, or thermoplastics in general or thermosetting resins.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific amniotomy devices discussed herein. Therefore, it is intended that this invention be limited only by the claims and the equivalents thereof.

What is claimed is:

1. An amniotomy device comprising:
a shaft comprising a rupture crown disposed along a distal end portion of the shaft, the rupture crown comprising a distal end defined by at least two leading bite wings and a recess formed in the distal end of the rupture crown between the leading bite wings, wherein the rupture crown is structurally configured to be atraumatically inserted into a cervical canal;
wherein the leading bite wings are structurally configured to atraumatically engage an amniotic membrane when the shaft is rotated.

2. The amniotomy device of claim 1, wherein a lateral cross-section of the rupture crown is substantially circular.

3. The amniotomy device of claim 1, further comprising:
at least one trailing bite wing formed on a side of the rupture crown;
wherein the trailing bite wing is configured to wrap the amniotic membrane onto the rupture crown.

4. The amniotomy device of claim 3, wherein the trailing bite wing comprises a groove formed in the rupture crown.

5. The amniotomy device of claim 4, wherein the groove comprises an auger defined by a helical groove formed in a surface of the rupture crown.

6. The amniotomy device of claim 3, wherein the trailing bite wing comprises at least one prong projecting from a side surface of the rupture crown.

7. The amniotomy device of claim 1, wherein the leading bite wings comprise a first pointed projection separated from a second pointed projection by the recess, each pointed projection comprising an exterior surface of the rupture crown and curved to extend around a portion of the rupture crown in a circular arc.

8. The amniotomy device of claim 7, wherein the first and second pointed projections extend around the distal end of the rupture crown in a circular arc such that the recess comprises an annular recess.

9. The amniotomy device of claim 7, wherein at least one of the leading bite wings comprise a serrated leading edge comprising a multiplicity of teeth.

10. The amniotomy device of claim 1, wherein the distal end of the rupture crown comprises a plurality of prongs extending from the rupture crown and axially aligned with the shaft, and the recess comprises a plurality of recesses, each recess disposed between two adjacent prongs.

11. The amniotomy device of claim 1, wherein the rupture crown comprises a cylinder and the leading bite wings comprise at least four radially extending bite wings, each bite wing comprising an exterior portion that defines a circular arc, the exterior portion of each bite wing terminating in a point.

12. The amniotomy device of claim 1, further comprising:
a tubular sleeve disposed over at least a portion of the shaft and selectively lockable to the shaft;
wherein the tubular sleeve is movable relative to the rupture crown between a first position in which the rupture crown resides within the tubular sleeve and a second position in which the rupture crown extends from the tubular sleeve.

13. An amniotomy device comprising:
a shaft comprising a rupture crown disposed along a distal end portion of the shaft, the rupture crown comprising a distal end, a recess formed in the distal end, and a pair of bite wings curved in a circular arc along an exterior boundary of the rupture crown, wherein the rupture crown is structurally configured to be atraumatically inserted into a cervical canal;
wherein the pair of bite wings are structurally configured to atraumatically grasp an amniotic membrane when the shaft is rotated.

14. The amniotomy device of claim 13, wherein each bite wing comprises a point formed between the distal end of the rupture crown and a slot formed in an exterior side of the rupture crown that communicates with the recess.

15. The amniotomy device of claim 14, wherein the distal end of the rupture crown is defined by the point of each bite wing.

16. The amniotomy device of claim 14, further comprising:
at least one trailing bite wing extending from the exterior side of the rupture crown.

17. An amniotomy device comprising:
a shaft comprising a rupture crown disposed along a distal end portion of the shaft, the rupture crown comprising a distal face, a plurality of prongs extending axially relative to the shaft from the distal face, and a plurality of axial recesses formed in the distal face of the rupture crown, each of the plurality of prongs disposed between two adjacent axial recesses, wherein the rupture crown is structurally configured to be atraumatically inserted into a cervical canal;

wherein the plurality of prongs are structurally configured to atraumatically grasp an amniotic membrane when the shaft is rotated.

18. The amniotomy device of claim 17, wherein each axial recess formed in the distal face of the rupture crown is open to an exterior surface of the rupture crown along an axial edge.

19. The amniotomy device of claim 18, wherein each axial edge of each axial recess formed in the exterior surface of the rupture crown comprises a trailing bite wing edge configured to engage the amniotic membrane.

* * * * *